(12) United States Patent
Thomas

(10) Patent No.: US 12,295,796 B2
(45) Date of Patent: May 13, 2025

(54) ADJUSTABLE SUPPORT

(71) Applicant: Andrew Thomas, Cheltenham (GB)

(72) Inventor: Andrew Thomas, Cheltenham (GB)

( * ) Notice: Subject to any disclaimer, the term of this patent is extended or adjusted under 35 U.S.C. 154(b) by 0 days.

(21) Appl. No.: 18/691,701

(22) PCT Filed: Sep. 20, 2022

(86) PCT No.: PCT/GB2022/052367
§ 371 (c)(1),
(2) Date: Mar. 13, 2024

(87) PCT Pub. No.: WO2023/041939
PCT Pub. Date: Mar. 23, 2023

(65) Prior Publication Data
US 2024/0374340 A1    Nov. 14, 2024

(30) Foreign Application Priority Data

Sep. 20, 2021 (GB) ...................... 2113413

(51) Int. Cl.
| | |
|---|---|
| *F16M 13/02* | (2006.01) |
| *A61B 90/35* | (2016.01) |
| *F21V 21/14* | (2006.01) |
| *F21W 131/205* | (2006.01) |

(52) U.S. Cl.
CPC ........... *A61B 90/35* (2016.02); *F16M 13/022* (2013.01); *F16M 13/027* (2013.01); *F21V 21/14* (2013.01); *F16M 2200/02* (2013.01); *F16M 2200/04* (2013.01); *F21W 2131/205* (2013.01)

(58) Field of Classification Search
CPC .... A61B 90/35; F16M 13/022; F16M 13/027; F16M 2200/02; F16M 2200/04; F21V 21/14; F21W 2131/205
See application file for complete search history.

(56) References Cited

U.S. PATENT DOCUMENTS

| | | | |
|---|---|---|---|
| 1,276,117 | A | 8/1918 | Riebe |
| 2,510,198 | A | 6/1950 | Tesmer |
| 3,546,961 | A | 12/1970 | Marton |

(Continued)

FOREIGN PATENT DOCUMENTS

| | | |
|---|---|---|
| EP | 3096065 A1 | 11/2016 |
| WO | 2011006502 A1 | 1/2011 |

OTHER PUBLICATIONS

International Search Report issued by ISA/EPO in connection with PCT/GB2022/052367 dated Mar. 23, 2023.

(Continued)

*Primary Examiner* — Evan P Dzierzynski
(74) *Attorney, Agent, or Firm* — Levenfeld Pearlstein, LLC

(57) ABSTRACT

An adjustable support arm system (10) comprises an anchoring arrangement (14) for mounting the support arm system (10) to a structure, an arm (18) carried by the anchoring arrangement (14) and comprising a plurality of arm segments (36) articulatable between several arm positions, the arm (14) being configured to support a device (120), and an immobilising mechanism operable between a free configuration permitting movement of the arm (18) and a locked configuration in which the arm (18) is immobilised, wherein the immobilising mechanism comprises a locking means to maintain the plurality of arm segments immobilised in the locked configuration.

16 Claims, 14 Drawing Sheets

(56) References Cited

U.S. PATENT DOCUMENTS

| | | | |
|---|---|---|---|
| 4,517,632 A | 5/1985 | Roos | |
| 4,692,850 A * | 9/1987 | LeDoux | F21V 21/02 |
| | | | 362/427 |
| 4,842,174 A * | 6/1989 | Sheppard | F16M 13/02 |
| | | | 224/567 |
| 5,165,786 A | 11/1992 | Hubert | |
| 5,375,049 A | 12/1994 | Witt | |
| 5,810,306 A * | 9/1998 | Hung | B25J 1/02 |
| | | | 362/419 |
| 7,481,404 B2 * | 1/2009 | Carnevali | F16M 11/40 |
| | | | 248/274.1 |
| 7,810,945 B2 * | 10/2010 | Mize | H01R 33/94 |
| | | | 439/642 |
| 2003/0184086 A1 | 10/2003 | Christianson | |
| 2009/0316426 A1 * | 12/2009 | Gilligan | A45C 15/06 |
| | | | 362/156 |
| 2011/0038064 A1 | 2/2011 | Xhunga | |
| 2019/0145473 A1 | 5/2019 | Puterbaugh et al. | |

OTHER PUBLICATIONS

Written Opinion issued by ISA/EPO in connection with PCT/GB2022/052367 dated Mar. 23, 2023.

* cited by examiner

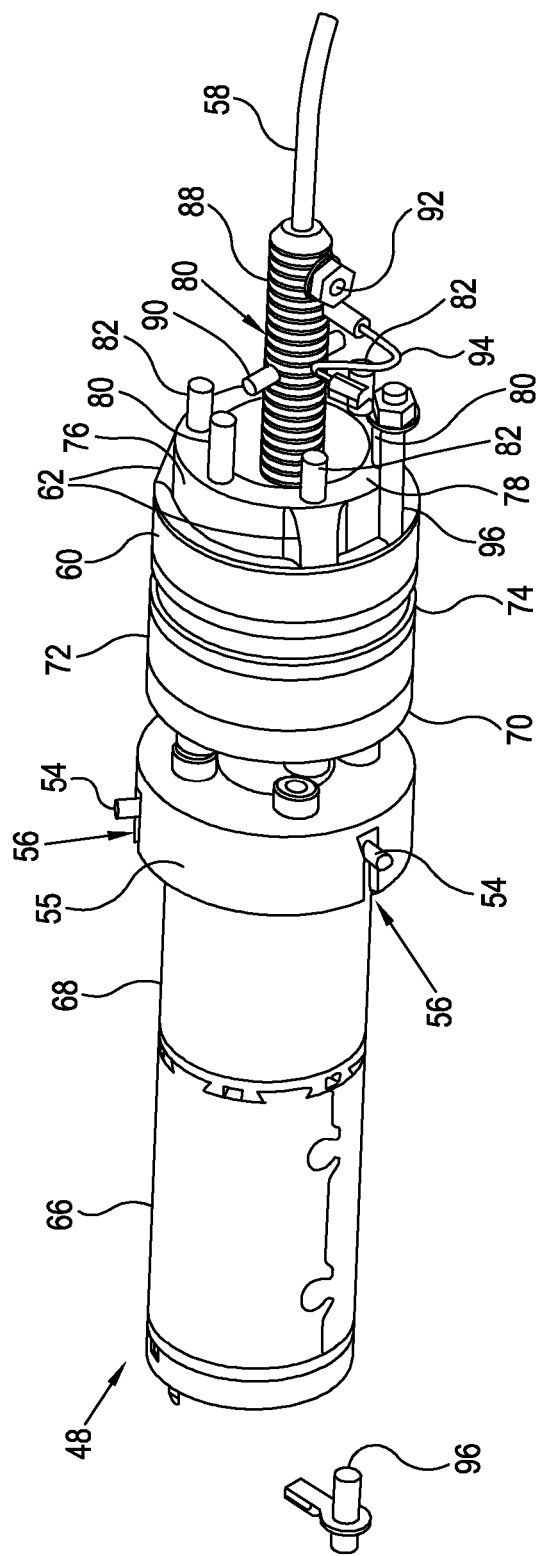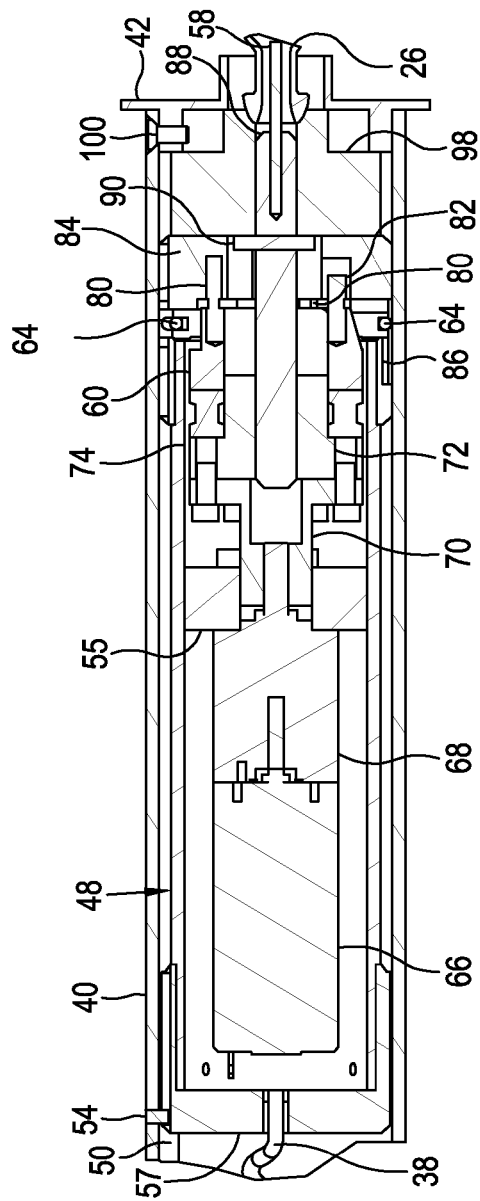
FIG. 5A
FIG. 5B

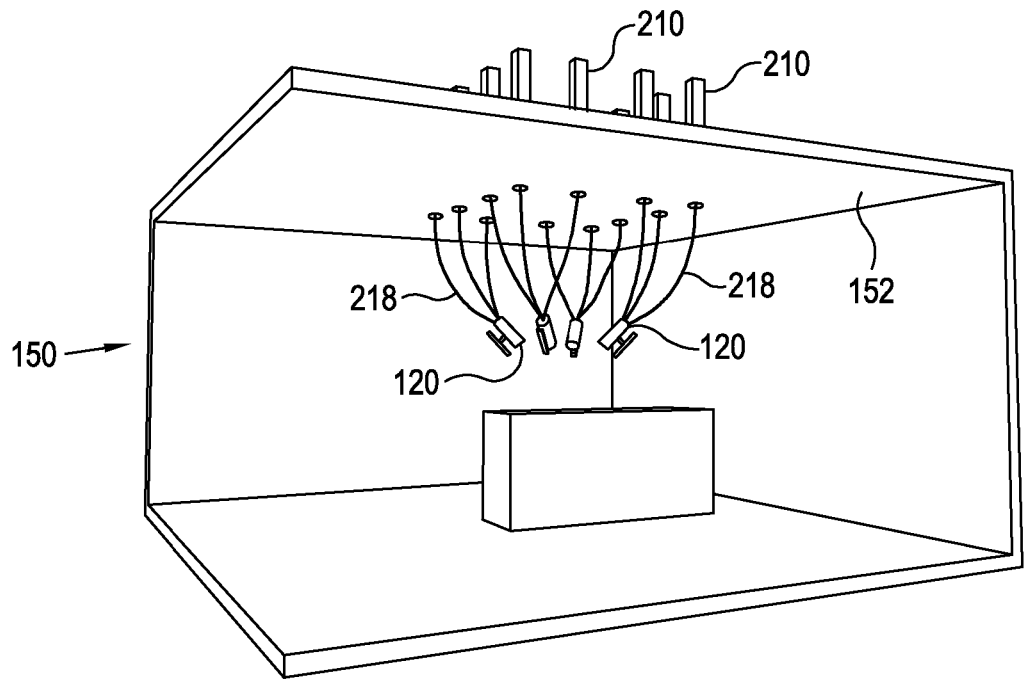
FIG. 11A
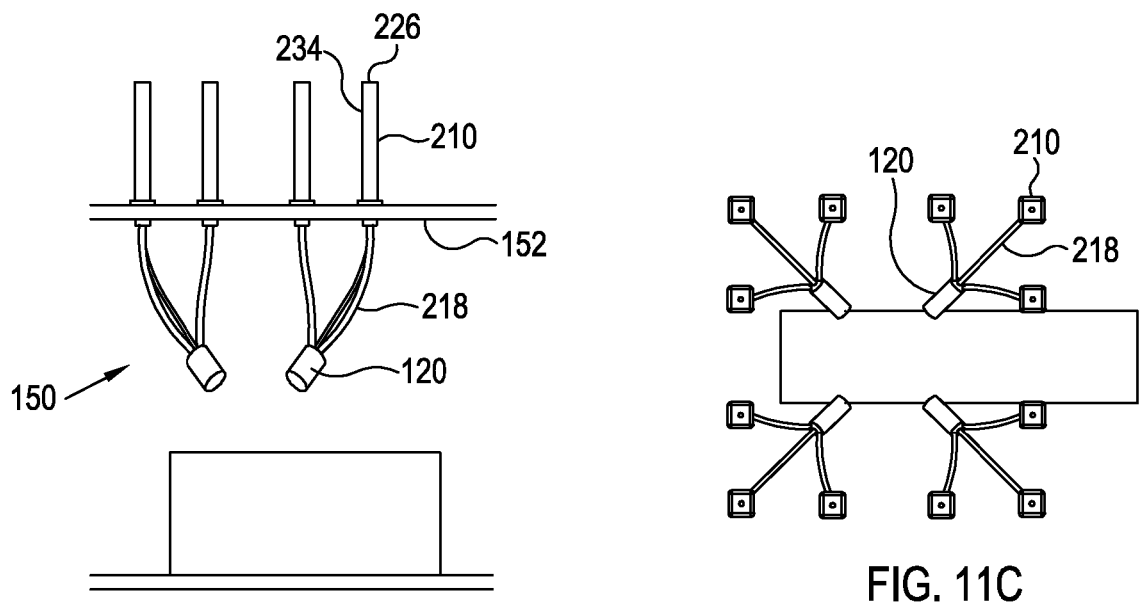
FIG. 11B
FIG. 11C

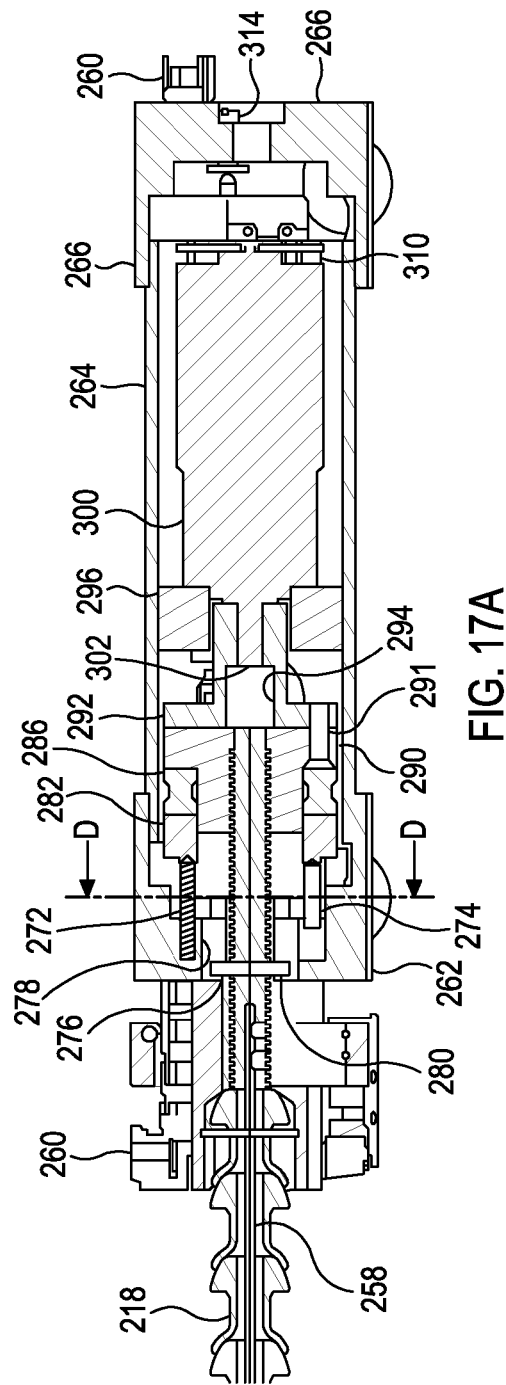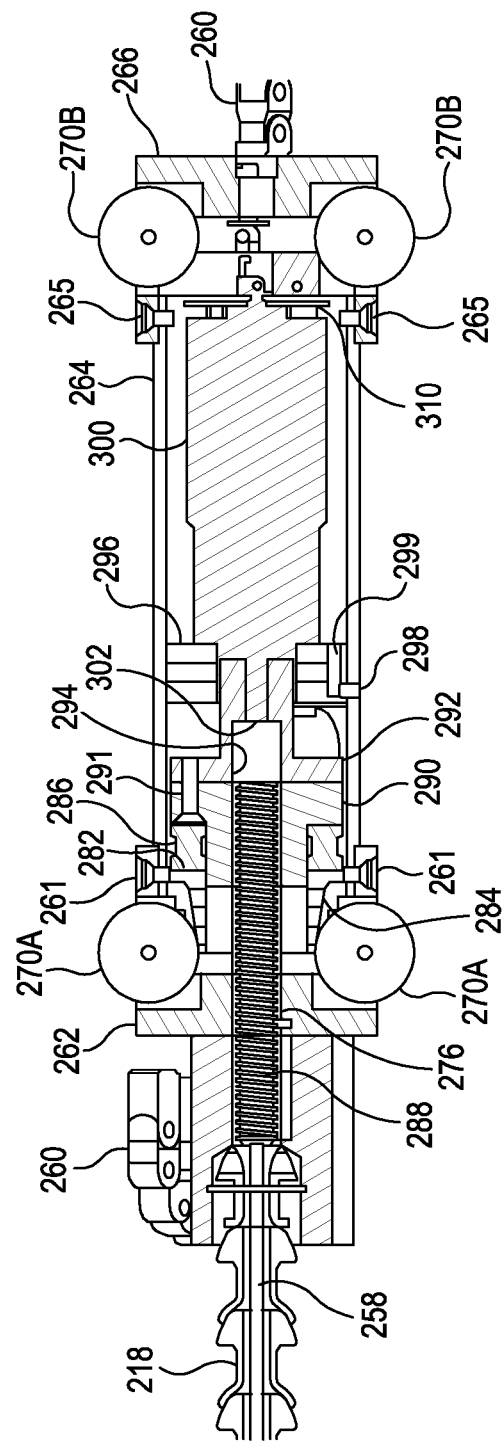
FIG. 17A
FIG. 17B

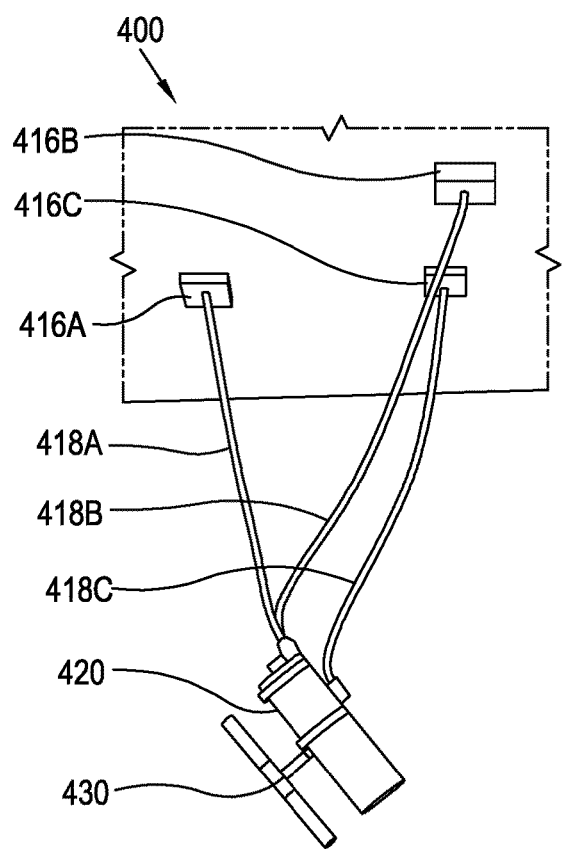
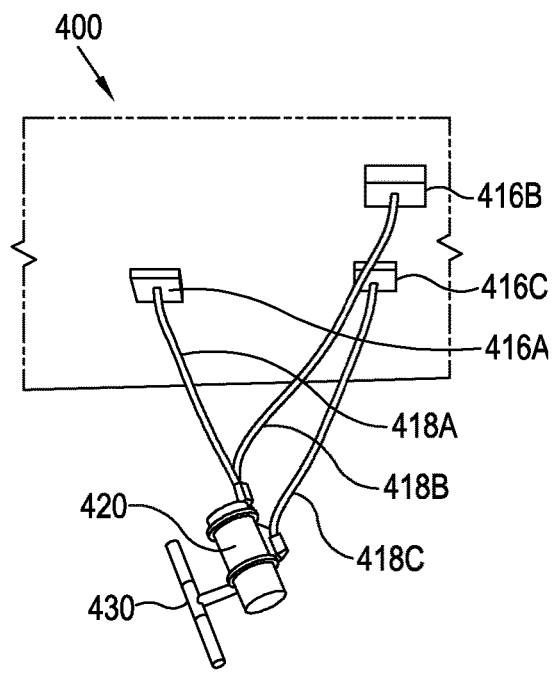
FIG. 19A
FIG. 19B

ADJUSTABLE SUPPORT

CROSS-REFERENCE TO RELATED APPLICATION DATA

This application is a 35 U.S.C. 371 U.S. national stage filing of International Application No. PCT/GB2022/052367, having an international filing date of 20 Sep. 2022, which claims the benefit of and priority to Great Britain Application GB 2113413.5, having a filing date of 20 Sep. 2021.

FIELD OF THE INVENTION

This invention relates to an adjustable support arm system. More specifically, but not exclusively, the invention relates to an adjustable support arm system for medical equipment, particularly to ceiling-mounted equipment such as operating theatre lamps.

BACKGROUND TO THE INVENTION

Operating theatres require bright, adjustable lighting so as to enable optimal illumination during surgery. Typical operating theatre lights comprise an array of lights on a dished lamp head, the array being spread out to reduce shadows by members of staff. However, such lamp types occupy a large amount of space in the operating theatre and can only illuminate the patient from one direction. In practice, such theatre lights are installed as sets of multiple lamps, which together are intended to provide even illumination regardless of staff movement.

The lights may be free-standing or mounted on a wall or ceiling of the room via a robust and often bulky support structure. The support structure generally comprises an arm comprising a series of fixed-length pivoting segments to allow the lights to be manoeuvred into various different positions. The lamps are relatively bulky and can be cumbersome to manoeuvre.

Modern operating theatres are also equipped with a ventilation system which directs ultra clean air into the operating room. The ultra clean air is usually arranged to flow downwardly into the room from the centre of the theatre ceiling in a linear manner, often arranged to flow over the patient to reduce the risk of contamination and infection. Bulky devices such as lamps and lamp arms may interfere with the air flow.

SUMMARY OF THE INVENTION

The Applicant has performed experiments to study the air flow beneath traditional operating theatre lights. In these studies, it was found that not only did the bulk of the lamp and its support structure interfere with the air flow, but the air flow actually rose beneath the lights in a turbulent manner. It is therefore an aim of the present invention to provide an adjustable mounting system that may help to ameliorate the above-mentioned problems.

According to a first aspect of the present invention there is provided an adjustable support arm system as defined by claim 1, comprising an anchoring arrangement for mounting the support arm system to a structure; an arm carried by the anchoring arrangement and comprising a plurality of arm segments articulatable between several arm positions, the arm being configured to support a device, and an immobilising mechanism operable between a free configuration and a locked configuration, wherein in the free configuration the immobilising mechanism permits movement of the articulatable arm, and wherein in the locked configuration the immobilising mechanism maintains the articulatable arm in one of the several arm positions, wherein the immobilising mechanism comprises locking means to maintain the plurality of arm segments immobilised in the locked configuration.

It will be understood that the support arm system is intended for mounting to a structure such as a ceiling, wall or similar, and may also be used with a freestanding support of sufficient mass. The arrangement allows a user to select a position of the articulatable arm and to fix it in the selected position by switching between the free configuration and the locked configuration.

In some embodiments, the support arm system comprises an actuator located at a location along the articulatable arm or at an end thereof, the actuator allowing the locking means to be released, to assume the free configuration.

Conveniently, the actuator is provided in the form of a trigger or trigger button on or near a handle portion. The handle portion provides a handle for a user to grip the articulatable arm to move it to readjust its position while the immobilising mechanism is in its free configuration, e.g. disengaged. It can be imagined that a trigger on the handle portion facilitates releasing the locking means as a user holds the handle. The configuration may be such that releasing the actuator causes the immobilising mechanism to resume the locked configuration to lock the articulatable arm in the selected position. This allows a user to hold and move the support the arm (and/or a device supported by the arm) via the handle in the desired position, practically singlehandedly. Once positioned, the immobilising mechanism is allowed to engage, to assume the locked configuration, when the user releases the actuator. Thereby, it is less likely that actuating the immobilising mechanism causes a re-positioning of the arm. The actuator may be made from, or comprise a surface of, a material that is readily cleanable and/or sterilisable, e.g. from metal or from another appropriate material. This allows the handle to be touched by members of a surgical team during surgery.

The arm comprises a plurality of arm segments connected in series to form a length of arm. The locking means of the immobilising mechanism allows the plurality of segments to be immobilised by way of a single actuation, to ensure the different segments are locked in position at practically the same time.

Embodiments of the invention therefore provide a mount which is capable of suspending an item from a support, which could be provided on a wall, stand or ceiling, and which is flexible to allow the item to be manoeuvred into a desired position before being locked in place to prevent unintentional further movement.

The device supported by the adjustable support arm system may be an operating theatre lighting or medical equipment such as microscopes or other imaging devices. It will be appreciated that the invention is not so limited and that the articulatable arm may be used to support any type of device, such as video and audio equipment (screens, speakers, computer displays, monitoring equipment), as well as trays, consoles or input systems, in a laboratory, engineering shop floor, food preparation lines and clean room environment etc., where equipment may need to be supported typically in an immobilised position yet may require repositioning from time to time.

In some embodiments, the arm is retractable at least partially or fully into a housing structure provided by the anchoring arrangement.

The anchoring arrangement may comprise a housing structure to partially or fully accommodate the support arm. The housing structure may be provided by a cavity of the anchoring arrangement. It will be appreciated that the arm may be fully retractable or partially retractable, in a gradual manner, such that part of the length of the arm, or portions of the arm, are locatable within the housing structure and other parts of the length of the arm or portions of the arm are located outside the anchoring arrangement. This reduces the amount of arm components outside the anchoring system, e.g. in a room. Therefore, if the arm-supported device is to be positioned closer to the anchoring arrangement, for instance higher up for a ceiling-mounted anchoring system, portions of the arm need not form a loop or other collapsed configuration outside the anchoring arrangement.

The retracting mechanism may be provided by a carriage mechanism such as a shuttle moveable within the anchoring arrangement to pull or push the articulatable arm inward or outward. The retracting mechanism may be provided by a reel mechanism.

The retracting mechanism may be operatively connected with the actuator such that, upon releasing the immobilising mechanism, the retracting mechanism is released to permit extension or retraction of the articulatable arm relative to the mounting arrangement.

In some embodiments, the anchoring arrangement comprises a stabilising system to maintain the arm in balance at different retraction positions. The stabilising system may be provided by a counterbalancing system, for instance in the form of weights, or in the form of a biasing system, for instance in the form of spring elements. The stabilising system provides that the arm, and the device carried by it, is practically self-supported and therefore moveable with similar force independent of how far it is retracted into the anchoring system. In practice, this facilitates the movement of a lamp, which may be at a relatively awkward position such as above-head height, as a user needs to only move the lamp into a desired position, without also having to support the weight of the lamp. This reduces the likelihood and practically avoids that portions of the arm slide or fall out of the anchoring arrangement, and only move outward (e.g., down) if pulled by a user. The stabilising system may balance the support arm, or alternatively may bias the arm into a retracted position or extended position in a controlled manner, e.g. a slow-moving retraction or extension, to avoid that the arm is either retracted to fast or falls from the anchoring system.

In some embodiments, the arm comprises a plurality of interconnected elements, connected in series to form a length of arm.

The plurality of arm segments may be constituted by a plurality of interconnected elements.

In some embodiments, articulatable elements of the arm are inside a skin structure. The arm may comprise a hollow sheath providing the skin structure extending along most or all of its length, extending over a plurality of individual articulatable segments of the arm. The sheath may exhibit a certain amount of flexibility so as to adapt the range of articulation of the arm. For instance, the skin structure may be extendable and contractible. The skin structure may be of a material that retains a smooth outer surface so that it is easy to clean or disinfect, for instance using wipes or other standard disinfectants found in a surgical setting.

In some embodiments, the interconnected elements are angularly disposable relatively to each other by ball joint connections.

The arm may comprise a plurality of interconnected elements which are arranged for relative movement therebetween to allow the arm to be articulated. Each one of the interconnected elements may comprise a protrusion at a first end and a protrusion-receiving socket at a second end, in the form of a ball joint or universal joint, the protrusion of one element being configured for articulated movement within the socket of an adjacent element. The interconnected elements may be of the same type. However, this need not necessarily be the case and some interconnected elements may be of a different shape, length, and connection geometry. The plurality of interconnected elements may be arranged as a so-called mechanical snake. It will be appreciated that the provision of ball joint connections allows adjacent segments to be angled isotropically, permitting the same degree of freedom relative to the axis of an adjacent element. However, other types of joint may be used in some embodiments.

In some embodiments, the interconnected elements comprise a channel passage for end-to-end connection of a series of interconnected elements.

In some embodiments, the channel passage extends axially within the interconnected elements.

In some embodiments, the interconnected elements are connected by a tensionalbe arrangement.

In some embodiments, the tensionable arrangement comprises a tensioning component such as a wire, cable, cord or the like, providing a locking means extending along the articulatable arm, conveniently through guide passages provided by channel passages extending axially through individual ones of end-to-end connected interconnected elements. It will be appreciated that the tensioning component is connected at opposite ends of the articulatable arm, for instance at one of the distal segments of the articulatable arm outside the anchoring arrangement, and within the anchoring arrangement, thereby providing an immobilising mechanism. Tightening of tensioning component brings the interconnected elements into tighter abutment, creating a degree of slip-inhibiting friction that impedes articulation of the interconnected elements relative to each other, and allows the arm to be practically locked in position. By slackening the tensioning arrangement, the interconnected elements are not restricted in this way, having a practically free configuration, and are thereby articulatable to reposition the arm. The tensioning component may be of any suitable material and strength that allows the interconnected elements to be pulled together and relaxed.

One end of the wire or cable may be attached to a reel or shuttle located in the anchoring arrangement that may be controllable to pull the wire, e.g. by winding or retracting it, to a position providing sufficient tension for immobilising the articulatable arm. Alternatively or in addition, the tension of the wire may be controlled by an actuatable lead screw or any other suitable mechanism.

The support arm system may comprise a retracting mechanism for extending and retracting the articulatable arm from the anchoring arrangement, and a tensioning arrangement for immobilising the articulatable arm and maintaining it in an immobilised condition. Thereby, the portion of the articulatable arm that is outside the anchoring arrangement is immobilised in a desired position. The retracting mechanism and the tensioning arrangement may be located in a common subassembly, such as a carriage providing the retracting functionality and the tensioning functionality.

In some embodiments, the anchoring arrangement comprises a motorised unit as part of the retracting mechanism and/or as part of the tensioning mechanism.

The motorised unit, such as a carriage, shuttle or reel may be configured for translation within the anchoring arrangement to thereby alter the extension of the arm (i.e. the portion of the articulatable arm outside the anchoring arrangement). In particular embodiments, the anchoring arrangement may comprise an elongate track structure along which the carriage or shuttle may travel. Some embodiments of the invention are intended for a vertical installation, in which anchoring arrangements have an elongate extension defined by the track structure for a shuttle. In that case, by orienting the anchoring arrangements upright, the elongate extension extends vertically. In such embodiments, a counterbalance mechanism may be provided to maintain the reel or shuttle in balance. Alternatively, the anchoring arrangement may be designed for installations in a horizontal orientation. In such embodiments, a biasing mechanism such as a spring mechanism may be provided to assist maintaining the reel or shuttle at a position along the track structure. The spring biasing mechanism may comprise a constant tension spring.

The anchoring arrangement and/or the articulatable arm may be configured to reduce their impact on air-flow within the room within which they are installed. Preferably, the anchoring arrangement is installed within (above) the ceiling, or close to the ceiling. When not completely concealable within a ceiling, the anchoring may comprise an outer housing, such as a round or aerodynamically shaped fairing, to reduce its impact on air flow. The articulated arm comprising a series of elements interconnected by a wire structure may be manufactured with a relatively small diameter, not exceeding 5 cm, 4 cm, 3 cm, or 2 cm. By providing a skin structure around the articulatable arm, the presence of interstitial spaces and gaps on the arm's outer surface can be reduced and practically eliminated. Thereby, the arm surface can be designed to be smooth and of relatively low cross-section, which further reduces its impact on air flow. A smooth surface may also facilitate cleaning and disinfection, for instance using wipes. For instance, prototypes have been made with a silicone material that is flexible, chemically inert and smooth. However, it will be appreciated that the invention is not so limited and that other materials may be used. The cross-section of the arm may be round so as to present the same (low) level of air flow interference regardless of its orientation.

In some embodiments, a plurality of anchoring arrangements and arms supports one device. In some embodiments, a plurality of, for instance three, articulatable arms is used to jointly support a single device. This allows relatively weaker or lower powered components to be used, e.g. lower specification motors, simpler balancing means and/or thinner arms, than might otherwise be the case, while still reliably supporting the device in an immobilised configuration. Embodiments with multiple articulatable arms may comprise a synchronised actuation system such that a single actuator can be used to switch between the free confirmation of all arms and the locked configuration of all arms. It will be understood that the number of articulatable arms may be chosen to suit the intended device to be supported, and may take into account both the weight and size of the device, and relative size and support capacity of the number of (one or more) arms. Relatively smaller devices such as LED lamps may require only a single support arm.

In some embodiments, the device is a lamp. The invention may be embodied by a lighting system comprising a lamp supported by an adjustable support arm system according to any one of the embodiments hereinbefore described.

BRIEF DESCRIPTION OF THE DRAWINGS

Exemplary embodiments of the invention will be described in more detail below with reference to the accompanying drawings, in which:

FIG. 5A is a view of a shuttle unit subassembly;

FIG. 5B is a cross-section view of the subassembly of FIG. 5A;

FIG. 11A is a perspective view of another installation, according to another embodiment;

FIG. 11B is a side view of the installation of FIG. 11A;

FIG. 11C is a top view of the installation of FIG. 11A;

FIG. 17A is a longitudinal cross-section along the line A-A in FIG. 12D;

FIG. 17B is a longitudinal cross-section along the line B-B in FIG. 12D;

FIG. 19A shows a photograph of a prototype in a first locked configuration; and

FIG. 19B shows a photograph of the FIG. 19A prototype in a second locked configuration.

DETAILED DESCRIPTION OF CERTAIN EMBODIMENTS

Figure 1A:
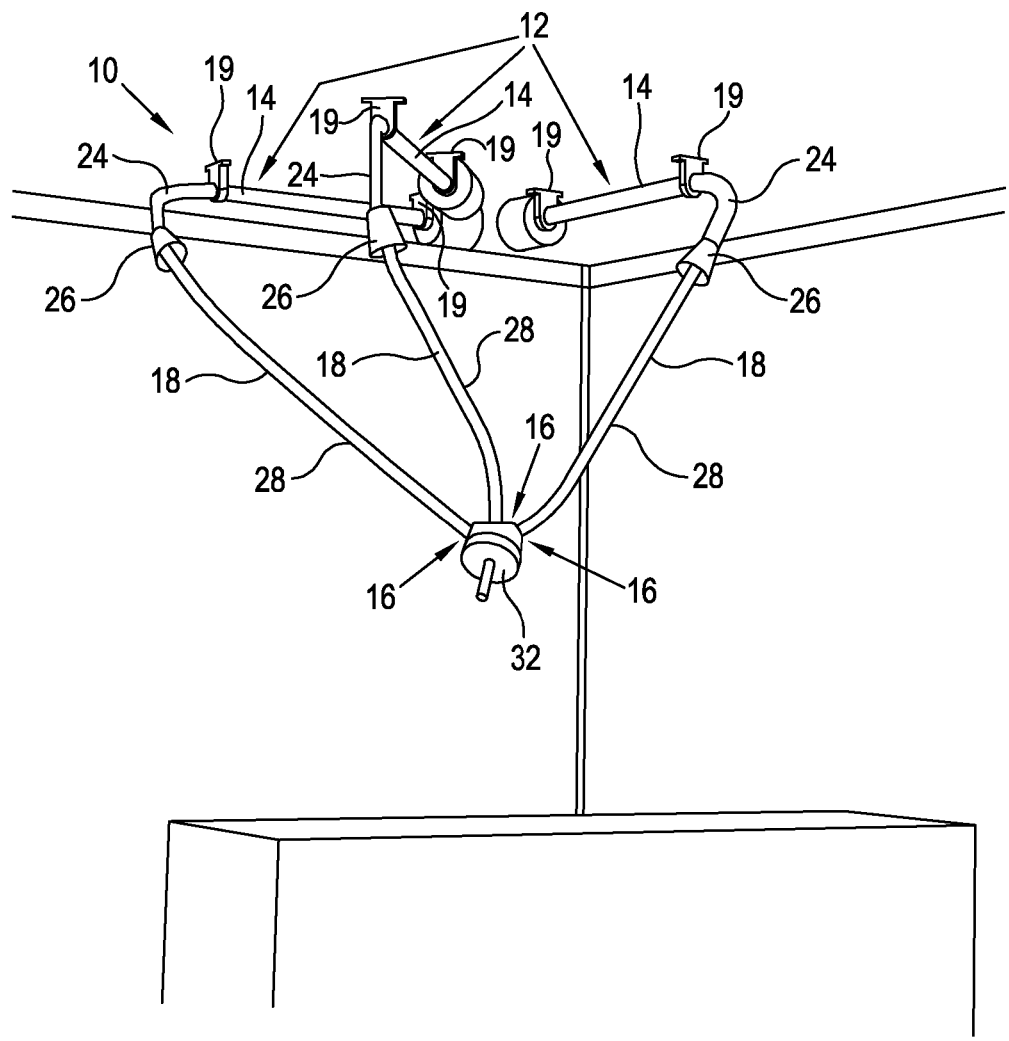
FIG. 1A is a perspective view of an embodiment.
Figure 1B:
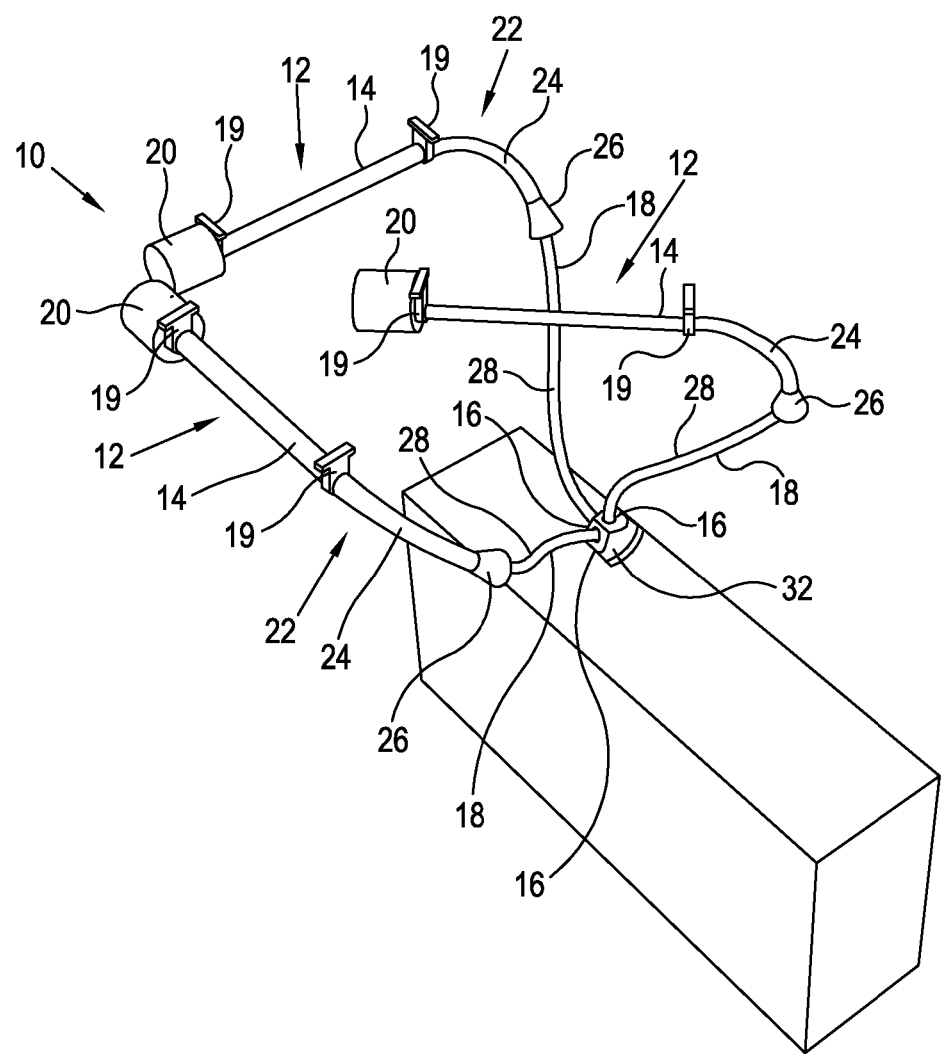
FIG. 1B is a top perspective view of the embodiment of FIG. 1A.

With reference to FIGS. 1A and 1B, there is illustrated a mounting arrangement 10 constituting an adjustable support system. The mounting arrangement 10 comprises three support arrangements 12. Each support arrangement 12 comprises a support 14 constituting an anchoring arrangement, a mount 16 providing a connection for, or constituting, a socket or receptacle structure 32 for a device to be provided (not shown), and articulatable arm 18 carried by and extending from the support 14 to support at a free end thereof the mount 16. Each support 14 provides a generally elongate housing structure with a cavity from which an articulatable arm 18 can extend.

The supports 14 are each mounted on a ceiling of an operating theatre room via a pair of support mounting brackets 19, one support mounting bracket 19 each provided at an end (front and rear) of the supports 14. The mounting arrangement 10 is located in a corner of the theatre room, wherein two supports 14 are arranged perpendicularly to each other extending generally parallel to the walls, and a third support 14 is located between the other two supports 14 at an angle of 45 degrees with respect to each of the other two supports 14. The supports 14 have a rear end facing, when installed, towards the corner of the room. The rear ends comprise a control box 20 which may contain control electronics, connections etc. The supports 14 each comprise a front end 22 comprising an opening via which the articulatable arm 18 extends. At the front end 22, the support 14 comprises a guide funnel 24, which may comprise a flexible tubular structure or sleeve as a guide channel from which the articulatable arm 18 extends. As illustrated, a free end of the guide funnel 24 is flared, of frusto-conically expanding form, providing a funnel opening 26 with an increased cross-section to provide freedom to bend the articulatable arm 18 in any lateral direction. It will be appreciated that the funnel opening may be round to allow isometric movement, or alternatively may have a different shape when it is intended to restrict movement in some directions.

Figure 2A:
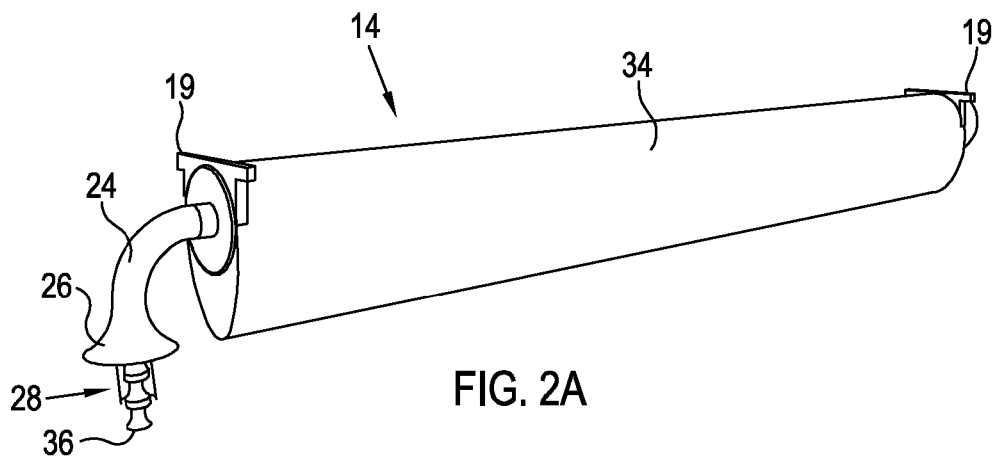
FIG. 2A is a perspective view from a first end of a component.
Figure 2B:
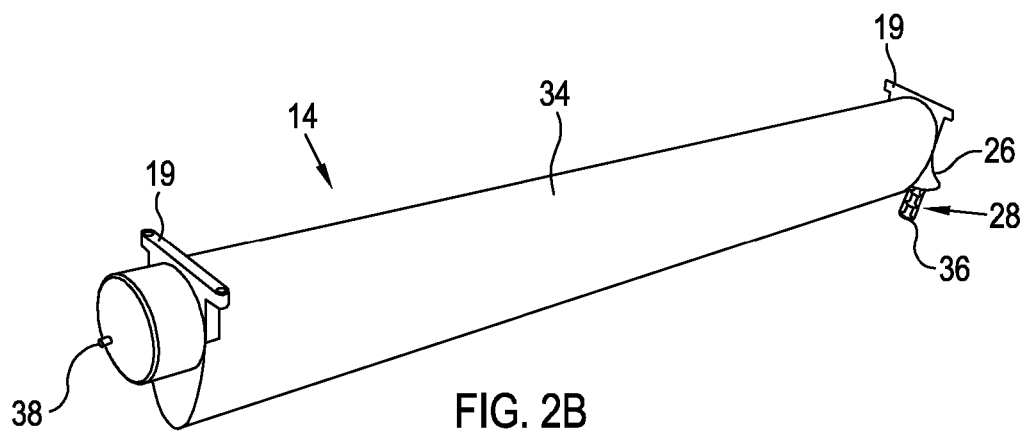
FIG. 2B is a perspective view from a second end of the component of FIG. 2A.
Figure 3:
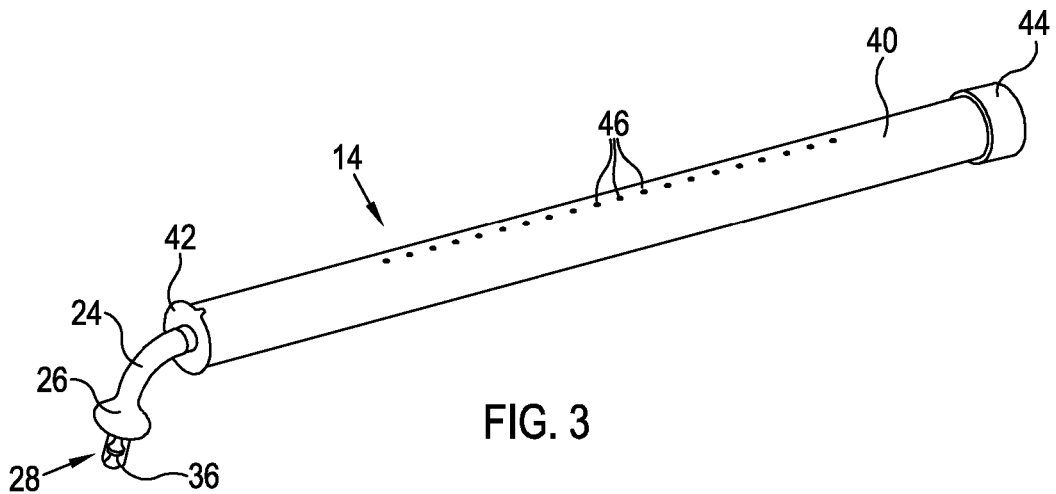
FIG. 3 is a perspective view of a subunit of the component of FIG. 2A.

FIGS. 2A, 2B and 3 show views of the support 14. Each articulatable arm 18 is articulatable by way of a series of interconnected elements 36 (see description of FIGS. 8A and 8B below) connected in series to form a length of arm 18, and articulatable relative to each other in the manner of a snake mechanism. The articulatable arms 18 are located within a sheath 28 providing skin structure surrounding the series of interconnected elements 36, providing a continuous outer surface of the articulatable arms 18 by covering interstitial spaces or gaps between the interconnected elements 36. The sheath 28 prevents the ingress or egress of contaminants, as well as reducing the risk of entrapment of foreign bodies between interconnected elements 36. The sheath 28 may be of any suitable materials such as a composite material. For instance, the outside of sheath 28 may be made from silicone rubber comprising on the inside a woven fibreglass lining. An outer silicone rubber prevents dirt ingress. Composite materials such as those comprising fibreglass or PTFE may provide low friction, reducing friction interference with the interconnected elements 36.

Each support arrangement 12 comprises an immobilising mechanism, which will be described in more detail below, operable to immobilise the articulatable arms 18 in a selected position. In the described embodiment, the immobilising mechanism is provided by a tensioning element in the form of a wire extending along (here: through) passages of the interconnected elements 36, the wire being retractable and extendable to thereby tighten or loosen, respectively, the surface-to-surface engagement between adjacent ones of the interconnected elements 36.

Conveniently, by providing a wire mechanism, the wire may be provided as a single actuatable element that can tighten or loosen multiple, and conveniently all, of the interconnected elements of one arm following actuation of a single control means, at practically the same time. When tightened, the interconnected elements 36 assume a locked configuration in which they are pushed against each other, in friction abutment relative to each other, immobilising the articulatable arm 18 in practically any configuration it had at the time of tightening the wire.

The mounts 16 are provided for affixing a device such as a theatre lamp. The mounts 16 may comprise a hub 32 to which end portions of each articulatable arm 12 connect such that mount may be carried by one or more (here: three) arms 12. The hub 32 may provide or carry a socket or retainer structure for a device to be mounted.

As shown in FIGS. 2A and 2B, the supports 14 may comprise an aero-dynamic fairing 34, extending along a length of each support 14, between the mounting brackets 19, i.e. practically from end to end. The fairing 34 is an elongate structure extending along a horizontal axis and has a generally ovally shaped contour in cross section so that air may flow smoothly in a downwards direction across the support 14. An aerodynamically shaped fairing is believed to reduce interference with the controlled clean air flow within the operating theatre. External connections and mains wiring such as a cable 38 (FIG. 2B) are located at the rear end of the support 14, facing away from the centre of the room.

Figure 4:
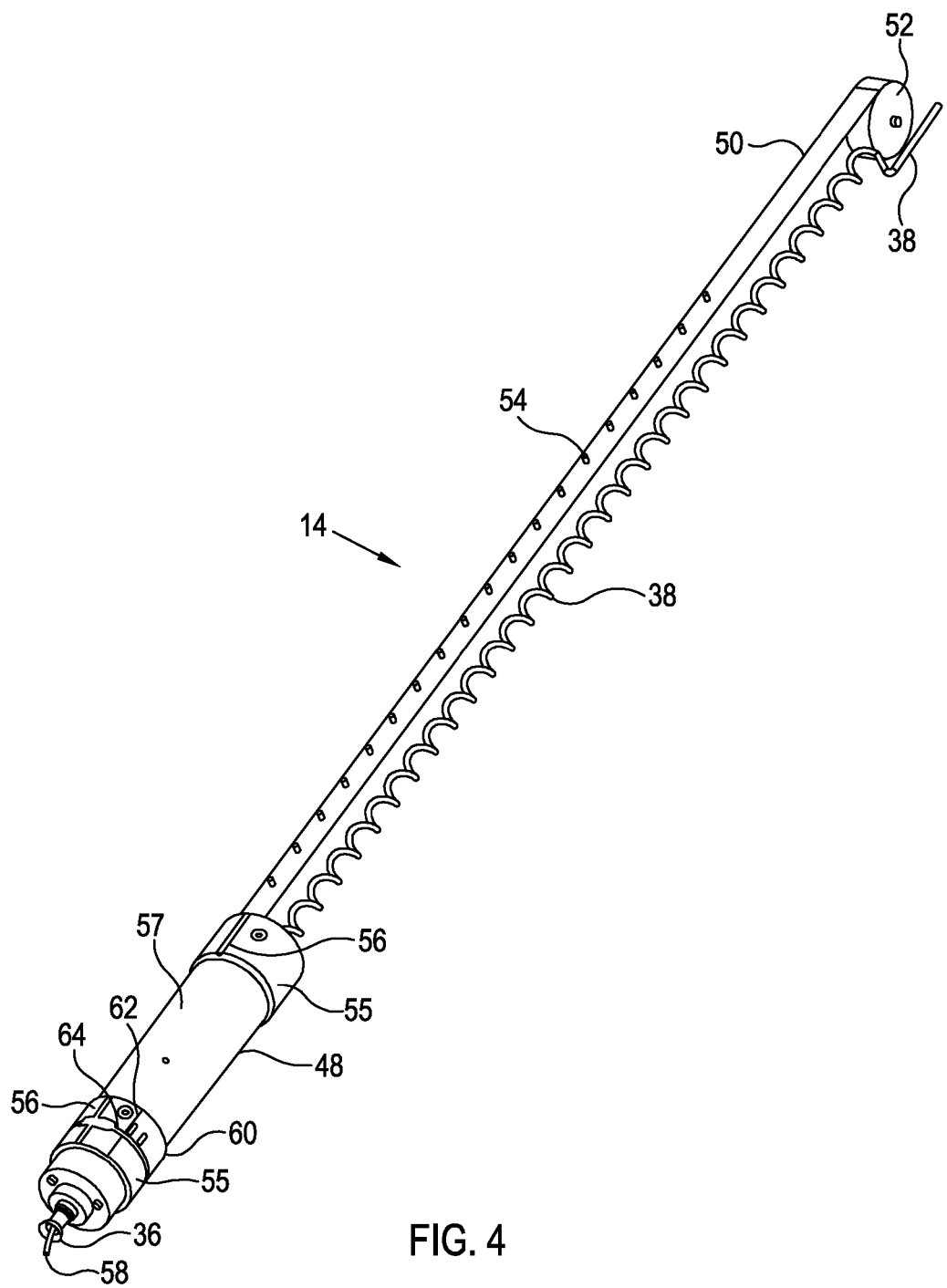
FIG. 4 is a perspective view of components of the FIG. 3 structure.

FIGS. 3 and 4 shows a retraction system and a tensioning system located in the housing structure provided by the support 14. The tensioning system comprises a cylindrical support tube 40 and end caps 42, 44, one of the end caps 42 providing an opening from which the tube 24 and guide funnel 24 extend as a channel for the articulatable arm 14. The support tube 40 is provided with a series of holes 46 arranged linearly spaced apart along the top surface.

FIG. 4 shows an internal mechanism of the retraction system and tensioning system, comprising a shuttle unit 48 constituting a carriage which is arranged to slide back and forth within the support tube 40 to thereby cause retraction or extension of the articulatable arm 18 from the support tube 40. A flat, constant force spring 50 is provided along the length of the support 14 and extends between the shuttle unit 48 and a rotatable wheel 52 disposed at a rear of the support 14. A series of guide pins 54 are provided in each of the holes 46 in the support tube 40 and a guide slot 56 is provided in anti-rotation collars 55 at a front and rear end of the shuttle unit 48 casing 57. The guide slot 56 is aligned with the guide pins 54 such that the shuttle unit 48 may travel within the support tube 40, while inhibiting and practically preventing rotation.

The cable 38 connecting to the control box 20 from the rear of the support 14 may connect directly to the shuttle unit 48. In that case, the cable 38 may be of coiled form, as shown, to allow it to extend and retract as required to follow the shuttle position. The cable 38 provides mains power for a motor provided within the shuttle unit 48, although it will be understood that other means of power supply, and/or other retraction means may be provided.

Turning to FIGS. 4, 5A and 5B, the shuttle unit 48 comprises at its front end a brake collar 60 that comprises three circumferentially spaced slopes 62 which are upwardly and rearwardly inclined so as to force a rubber brake band 64 radially outwardly against an inner surface of the support tube 40 to thereby friction-lock the shuttle unit 48 in position. Thereby, the shuttle unit 48 can be retained relatively securely, passively, without requiring shuttle motion or motor actuation. The friction fit between brake band 64 and support tube 40 can be established at any position along the tube, avoiding the need for graduated engaging mechanisms, while providing a sufficiently strong retention also for heavier devices. It will be understood that the friction force may be influenced by the choice of materials, number of brake pads and contact area, to suit the requirements of a device to be mounted.

Details of the shuttle unit 48 will now be described with reference to FIGS. 5A and 5B. Housed within the casing 57 is a motor 66 and gearbox 68. A second and third set of guide pins 54 are provided in rows spaced around the support tube for engagement in further slots 56 provided in each of the anti-rotation collars 55, as exemplified in FIG. 5A. A coupling 70 is provided between the gearbox 68 and a leadscrew nut 72, and a thrust bearing 74. The brake collar 60 is provided with its three slopes 62 mounted on a recessed cylindrical mantle surface 76. An end face 78 of the mantle surface 76 is provided with three circumferentially spaced-apart longitudinal springs 80 and three longitudinally extending pins 82. A brake cap 84 comprises recesses for location of the springs 80 and the pins 82. The brake cap 84 has an annular skirt 86 which extends over the brake collar 60. An underside of the skirt 86 is located relative to the slopes 62 to push the brake band 64, which is located in a groove in an outer surface of the skirt 86, into contact with the inner surface of the support tube 40 to thereby lock the shuttle unit 48 in position within the support 14.

The tensioning of the wire 58 may be achieved by a leadscrew 88, having a 10 mm diameter and a 2 mm pitch, that extends axially through the brake collar 60 and brake cap 84. The leadscrew 88 comprises a transverse anti-rotation pin 90. The wire 58 is connected to the leadscrew 88 and is held in position by a transverse clamp screw 92. An electrical wire 94 (for providing mains power to the lamp) is directed via the leadscrew 88 to permit connection via front and rear screws 96 to the casing 57.

A shuttle end cap 98 is positioned at the end from which the funnel end 26 extends. The end cap 98 includes a slot which engages with the anti-rotation pin 90. The first of the interconnected elements 36 of the articulatable arm 18 is arranged to project from the shuttle end cap 98, with the wire 58 passing therethrough. The shuttle unit 48 is axially retained within the support tube 40 by the end cap 42 which is attached to the support tube 40 via a transverse screw 100.

The motor 66 is configured to act on the leadscrew nut 72. Because the leadscrew 88 is prevented from rotating by the anti-rotation pin 90, the leadscrew nut 72 can be advanced by motor torque towards the thrust bearing 74, which pushes the slopes 62 against the skirt 86. As the slopes 62 advance, they splay the rubber brake band 64 which increases the friction and locks the shuttle unit 48 in position. This arrangement is advantageous because it avoids relative rotation of the leadscrew 88. This allows wiring to be connected laterally to the lead screw 88. Furthermore, the leadscrew 88 may be used for tensioning the articulatable arm 16 by retraction of the wire 58 in a linear manner, avoiding forces acting rotationally to cause repositioning of the articulatable arm while it is being tensioned.

Once the slopes 62 abut against the skirt 86, the lead screw nut 72 cannot further advance within the shuttle 48. Further rotation by the lead screw nut 72 thereby pulls the lead screw 88, which is prevented from rotation by the anti-rotation pin 90, back into the shuttle 48 (i.e., the lead screw nut 72 continues to advance relative to the lead screw 88). Thereby, the wire 58 is pulled backwards, resulting in a tightening of the interconnected elements 36. The arrangement is exemplary and allows gradual retraction and thereby tensioning on the basis of a small-pitch lead screw while avoiding rotation of the lead screw. The arrangement achieves that the retraction mechanism operates sequentially before the tensioning mechanism, allowing a carriage to retract the articulatable arm 12 until the tensioning mechanism engages to immobilise the articulatable arm 12 in a retracted position. While other mechanisms may be used to effect retraction and tensioning, it will be appreciated that it is beneficial to control the locking sequence such that the retraction mechanism operates before the tensioning mechanism, to provide that the arm remains flexible for retraction. It will be appreciated that loosening of the arrangement is achieved by appropriate operation of the mechanism in the reverse order.

Figure 6:
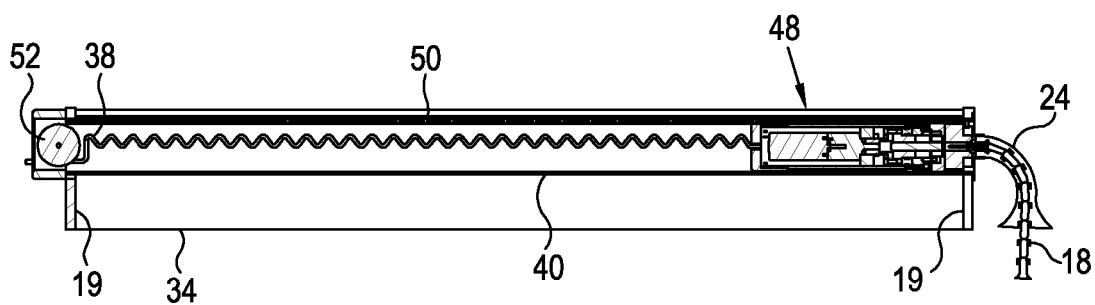
FIG. 6 is a longitudinal cross-section view of the structure of FIGS. 2A and 2B.

FIG. 6 shows a cross-sectional view of the support 14. The shuttle unit 48 is located at one end of the support tube within the fairing 34. The spring 50 and coiled cable 38 extend from a rear of the support 14, which also houses the wheel 52.

Figure 7:
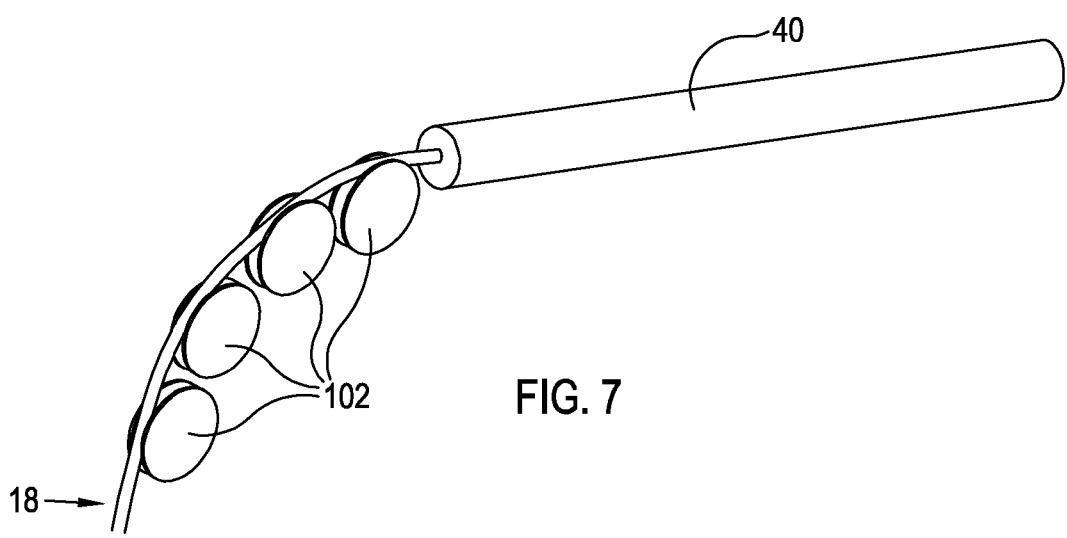
FIG. 7 is an illustration of a guide mechanism used in embodiments of the invention.

FIG. 7 illustrates a variant comprising an arrangement of guide wheels (here: four guide wheels 102) that may be provided to guide the articulatable arm 18 through the tube 24 and into the support tube 40. Accordingly, the guide wheels 102 may be mounted at a suitable position relative to the tube 24.

Figure 8A:
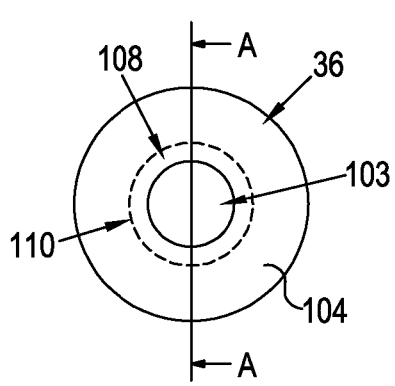
FIG. 8A is an end view of an interconnecting element.
Figure 8B:
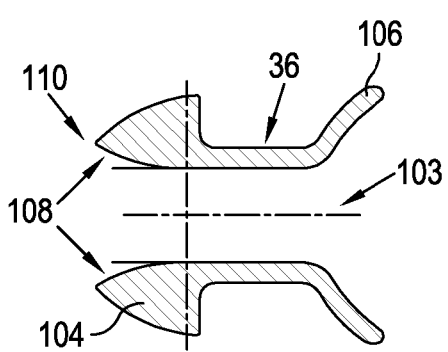
FIG. 8B is a cross-section of the interconnecting element of FIG. 8A.
Figure 9A:
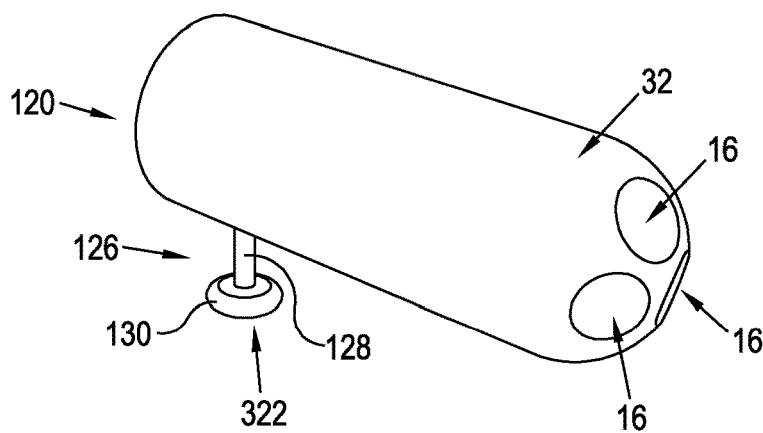
FIG. 9A is a rear perspective view of a lamp.
Figure 9B:
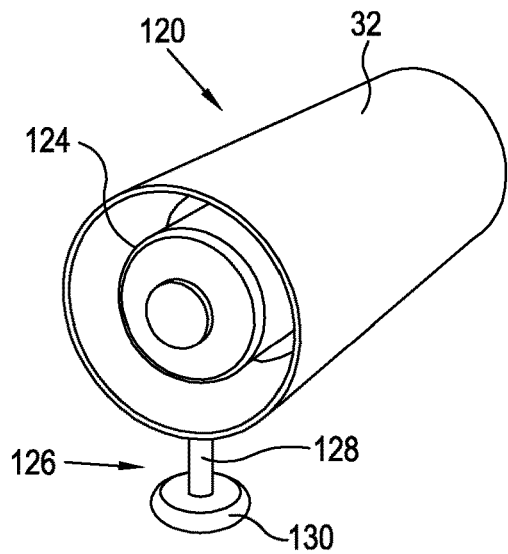
FIG. 9B is a front perspective view of the lamp of FIG. 9A.
Figure 9C:
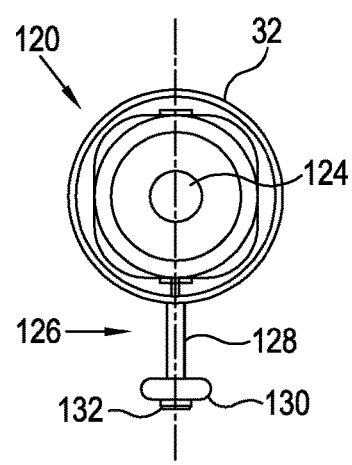
FIG. 9C is a front end view of the lamp of FIG. 9A.
Figure 9D:
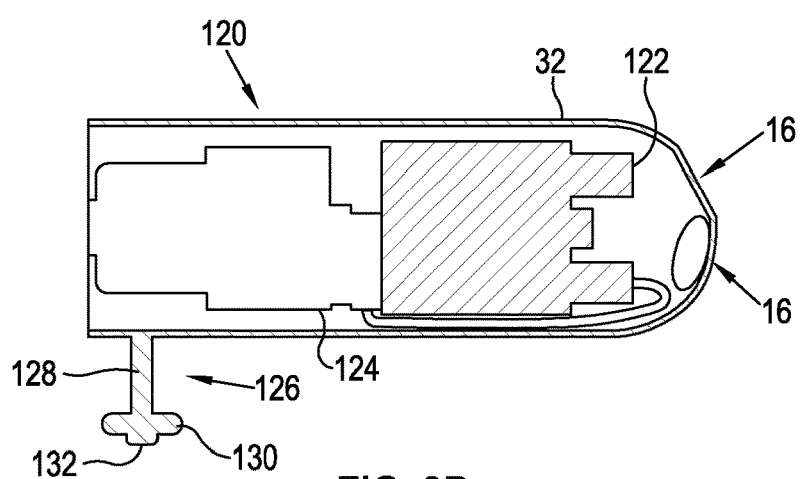
FIG. 9D is a cross-section view of the lamp of FIG. 9A.

FIGS. 8A and 8B show end and section views of an interconnectable element 36 employed in the articulatable arm 18. Each interconnectable element 36 has a generally cylindrical passageway 103 for the wire 58 to pass through, a domed joint 104 in the form of a rounded nose 110 at a first end and a socket 106 at a second end which is configured for receiving the domed joint 104 of an adjacent element 36. The interconnecting elements constitute arm segments. The radius of curvature of the domed joint 104 and the socket 106 are substantially similar, in the manner of a ball joint, so that one element 36 may be articulated isotropically with respect to its adjacent element 36, to allow the articulatable arm 14 to be articulated between several arm positions. At the nose 110 end, the passageway 103 comprises a flared mouth 108. The flared mouth 108 avoids pronounced edges at the end-to-end contact between two elements 36, thereby provides a channel surface that is rounded along the axial direction, reducing interference with the wire 58 when two adjacent interconnecting elements 36 are in an acutely angled end-to-end configuration.

The snake arrangement of FIGS. 8A and 8B is economical to manufacture because each of the interconnecting elements 36 may be of the same shape. This allows practically any suitable length of an articulatable arm 14 to be provided by selecting an appropriate number of interconnecting elements 36, the remaining operating principle to control tension of the articulatable arm 14 remaining the same. It will be appreciated that other arrangements are possible. For instance, in embodiments, interconnecting elements of different length may be used. The articulatable arm 18 may comprise two alternative elements, one having two sockets, the other having two nose ends, arranged in an alternating manner. Likewise, the elements may be provided in the form of a tube the ends of which provide two sockets, and a spherical element to engage between two tube ends. The tube and spherical element can be arranged in an alternating manner to form the articulatable arm 18.

Preferably, the cross-section of the passageway 103 is not much greater than the thickness of the wire 58 in order to provide a close fit of the wire within the passageway 103. Thereby, it can be achieved that the centreline of the wire 58 follows the centre line of the passageway 103 as closely as possible, and the wire 58 follows the shape of the articulatable arm by bending rather than lateral repositioning. This is to reduce the likelihood of a slack connection which can result in undue movement of the elements 36, e.g. by slippage, which in turn may lead to an unwanted loss of tension in the articulatable arm 18, or longer tensioning times that might otherwise have to be tolerated if the tensioning mechanism, such as the lead screw, requires more travel time than would otherwise be the case.

Turning to FIGS. 9A to 9D, these shows a lamp body 120 constituting an exemplary operating theatre light for use with the mounting arrangement 10 described above. The lamp body 120 is to be mounted to the hub 32 which is to be located on the mounts 16 of the three articulatable arms 18. Internal components 122 may be distributed within the lamp body 120 in a balanced manner, for instance towards the rear of the hub 32.

In the prototype depicted in FIGS. 9A-9D, a xenon projector 124 is provided as a light source at one end of the lamp body 120 to project a beam of light. The lamp body 120 comprises a handle 126 comprising a downwardly depending post 128 and a circular transverse finger plate 130 at a distal end thereof. An actuator button 132 is provided on the free end of the plate 130.

The actuator button 132 is operatively connected with the immobilising mechanism of the mounting arrangement 10. In the described embodiment, the actuator button 132 is in a rest position in which it maintains a locked configuration, and actuatable, e.g. by pressing the actuator button 132, to release the immobilising mechanism to assume the free configuration. It will be understood that actuation of the button 132 may cause a control signal to be sent, e.g. via wiring, to control the shuttle unit 48 to trigger relative movement of the brake collar 60 and brake cap 84, allowing the springs 80 to urge the brake cap 84 in a retracted position, whereby the annular skirt 86 is pushed away from the rubber brake band 64 which in turn disengages the support tube to thereby permit the shuttle unit 48 to move along the support tube 40 under the bias of the spring 50. In this embodiment, the immobilising mechanisms of all three of the supports 14 will be deactivated to set a free arm configuration when the actuator button 132 is pressed. In the free configuration, the springs 50 assist in balancing the weight of lamp body 120 to allow a user to easily move the lamp body 120 within the operating theatre space without having to also carry the weight of the articulatable arms 18. Each one of the articulatable arms 18 is also allowed to retract into (or extend out of) the support tubes 40 as the shuttle unit 48 moves towards the rear (or front) of the support 14 so as to shorten (or lengthen) the externally located portion (external of the housing structure) of articulatable arm 18 and thereby raise (or lower) the lamp body 120 if desired.

Once the lamp body 120 is in its chosen position, the user may release the actuator button 132, triggering the immobilising mechanisms of the mounting arrangement 10. To this end, each shuttle unit 48 is locked in position by engagement of the brake collar 60 and brake cap 84 with the rubber brake band 64, resisting movement of the shuttle units 48. The lead screw mechanism pulls the wire 58 to thereby tighten an abutment between all of the interconnected elements 36 and therefore causes the articulatable arms 18 to immobilise in their new positions.

Although a xenon projector 124 is described above, it will be appreciated that any appropriate light source may be used, such as LED light sources or others. The lamp body 120 may incorporate the controls for the light source, such as an on/off switch, brightness, focus, or colour controls.

The light controls, as well as the actuator button 132, need not be integral with the handle 126 as shown in FIGS. 9A to 9D. For instance, the light control switches and release mechanism may be controlled remotely, e.g. by a foot switch or it may be incorporated with other control units.

The external surfaces of lamp body 120 may be designed to facilitate their cleaning and disinfecting. The external surfaces may be smooth and avoid recesses or sharp corners. Components of the lamp body may be made from inert material. Individual components, such as the handle 126, may be removable and replaceable to facilitate their sterilisation off site.

Figure 10:
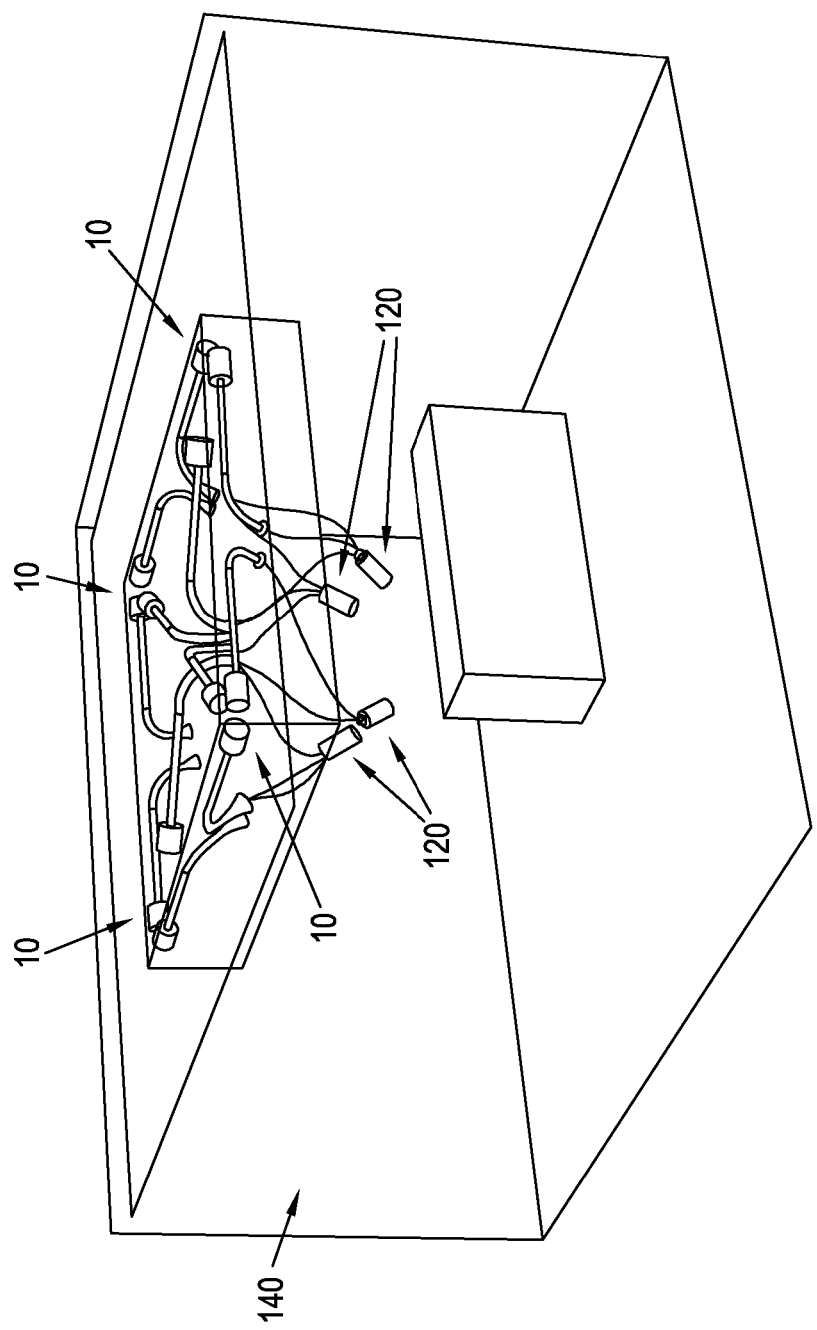
FIG. 10 shows a perspective view of an installation using embodiments of the invention.

FIG. 10 illustrates an installation 140 comprising four mounting arrangements 10 in an operating theatre 140 so as to provide four positionable lamp bodies 120. Each lamp body 120 may be independently manoeuvred to a desired position, in the manner described above. By providing four lamp bodies, two pairs of lamps are provided, one lamp body 120 may be located above each shoulder, i.e. on both sides of the heads, of a surgeon and an assistant. The arrangement of a snake mechanism using interconnected elements 36, immobilisable by a tensioning arrangement in the form of a wire, allows relatively thin support arms to be provided. This reduces their impact on air flow within the operating theatre environment. The impact on airflow is further reduced by providing retractable arms to reduce the length of the external portions of the support arms in the theatre room.

FIGS. 11A, 11B and 11C, show another embodiment, comprising supports 210 arranged for vertical mounting. Each support 210 is oriented upright to be installed in a space above a ceiling 152 of a room such as an operating theatre 150. Three supports 210 are provided as a mounting arrangement to support a lamp body 120 via three articulatable arms 218. Four such arrangements are provided to surround the work area of an operating table.

Figure 12A:
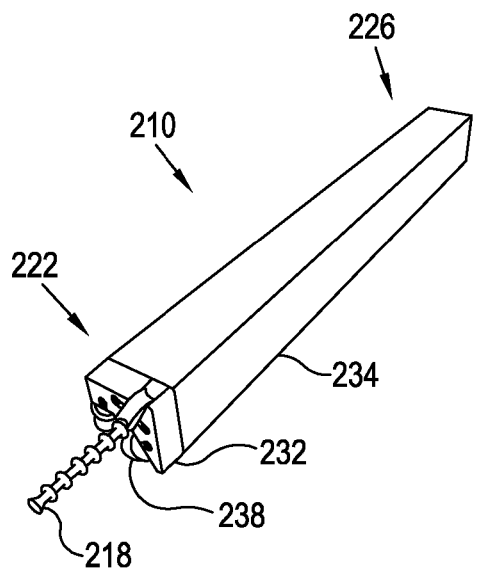
FIG. 12A is a top perspective view of an anchoring arrangement according to another embodiment.

FIG. 12A shows a support 210 for vertical mounting as illustrated in FIG. 11A. The support 210 comprises a housing 234 having a rectangular (here: square) cross-section containing a support mechanism described below. The housing 234 comprises a front end 222 with a front cap 232 providing a carrier structure on which three guide wheels 238 are rotatably disposed and between which an articulatable arm 218 is retractably disposed, the articulatable arm being provided with a sheath 228 constituting a skin structure. The front cap 232 corresponds in size and diameter to the cross-section of housing 234. Opposite the front end 222, the housing 234 comprises a rear end 226 configured with ports and the like as access for power supply and/or control systems. A rear end cap 236 (omitted in FIGS. 12A to 12C for clarity, shown in FIG. 15) covers the rear end 226. The rear end 226 constitutes a top end when the support 210 is installed vertically.

Figure 12B:
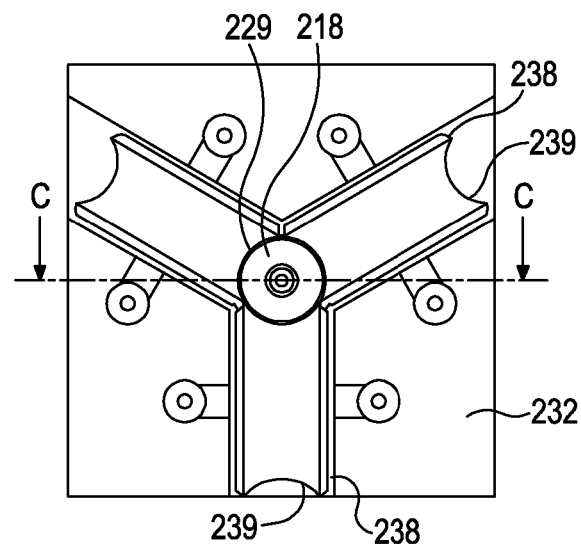
FIG. 12B is a front end view of the anchoring arrangement of FIG. 12A.

FIG. 12B shows an end view (when installed, an underneath view) of the front cap 232, showing three equiangularly radially spaced apart guide wheels 238 constituting a guide mechanism disposed in the front cap 232. The guide wheels 238 correspond to the guide wheels 102 of the aforementioned embodiment. Each guide wheel 238 comprises a concave running surface 239. The concavity of the running surface 239 matches a curvature 229 or portion (here: about a third) of the circumference the sheath 228 of each articulatable arm 218. Thus, the guide wheels 238 provide a contact surface to surround each articulatable arm 218, thereby constituting the guide mechanism for the articulatable arm 218 as it is extended from or retracted back into the support housing 234. The vertical arrangement allows an articulatable arm to be angled practically equally in any direction relative to the front cap 232.

The diameter of the guide wheels 238 is chosen to fit within the cross-section footprint of the front cap 232 and the housing 234 of the support 210. This helps to install the support 210 relatively flush with a ceiling surface, as indicated in FIG. 11B, because any apertures required in the ceiling 152 can be arranged with reference to the size of the support 210. Furthermore, the vertical installation allows practically the entire support mechanism, apart from the articulatable arm 218, to be retained above (within) the ceiling. This reduces and practically eliminates an impact of the support 210 on air flow below the ceiling 152. It will be appreciated that many operating theatres may be designed with an above-ceiling cavity suitable for accommodating installations of this type.

Figure 12C:
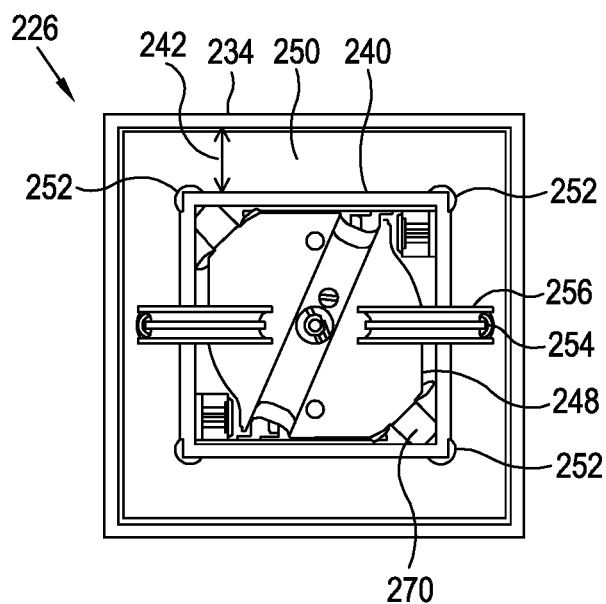
FIG. 12C is a rear end view of the anchoring arrangement of FIG. 12A.
Figure 12D:
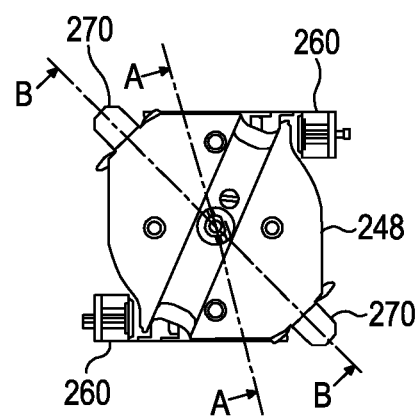
FIG. 12D is a view of selected components illustrated in FIG. 12C.

FIG. 12C shows an end view of the rear end 226 (in use: top end) of the support 210 without the rear cap 236, to better depict the inside of the support 210. Encased by the housing 234 is a quadrilateral support tube 240. The interior cavity of the support tube 240 provides a channel in which a shuttle unit 248 is translatably disposed. The shuttle unit 248 is conceptually similar to the shuttle unit 48 of the above horizontally-mountable embodiment. For clarity, the shuttle unit 248 is reproduced in FIG. 12D without the support tube 240. With reference to FIG. 12C, the outer cross-section of the support tube 240 is smaller than the cross-section of the housing 234. By locating the support tube 240 coaxially within the housing 234, a gap 242 remains that extends circumferentially between the support tube 240 and the housing 234.

The gap 242 provides a void suitable for accommodating a moveable counterweight 250 constituting a balancing means or counterbalance, constituting part of a stabilising system, here of generally quadrilateral contour with a quadrilateral hole, to fit within the gap 242 and around the support tube 240. The counterweight 250 is moveable along the outside of the support tube 240 while remaining retained within the contour of the housing 234. The inner corner edges 252 of the counterweight 250 are concavely recessed along the length of the counterweight 250. This is to reduce the risk of the counterweight 250 seizing up against the outer edges of the support tube 240. The counterweight 250 depends from an arrangement of (here: two) wires 254 each of which is suspended from a pulley 256 and at its inner end attached to the shuttle unit 248. The mass of the counterweight 250 may be larger than that of the shuttle unit 248 so that, when the support 210 is installed in its upright position, the shuttle unit 248 is slightly biased upward by the counterweight 250 weighing down and, by way of the wire 254, pulling up the shuttle unit 248.

Figure 13:
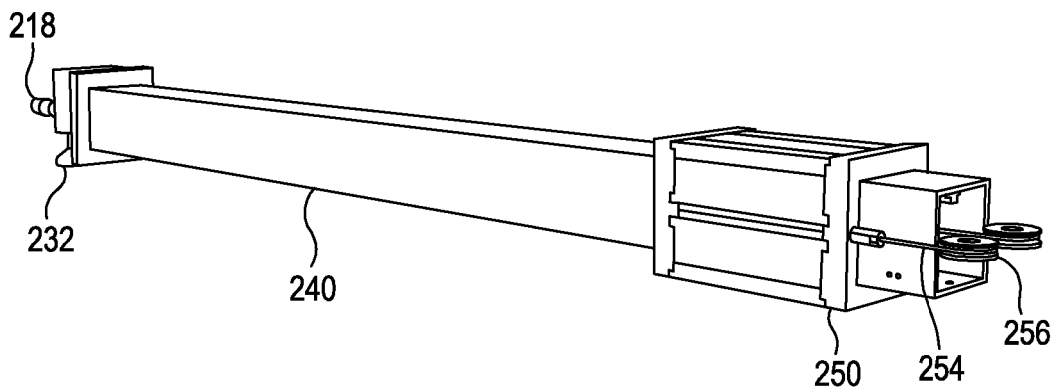
FIG. 13 is a rear perspective view of components of an anchoring arrangement.

FIG. 13 shows the support 210 without the housing 234 and the end cap 236, providing a view of the exterior of the support tube 240 and the counterweight 250. The support tube 240 comprises side walls suitable as track to allow the counterweight 250 to slide back and forth (i.e., when installed: up and down) along a length of the support 210. The side walls of the support tube 240 may be generally flat and featureless, as shown, and/or may comprise guide structures such as grooves or ribs. It will be appreciated that the cross-section of the housing 240 may be other than quadrilateral, and that the counterweight 250 need not necessarily surround the housing 240. However, the present configuration is a simple design solution allowing the components of the support mechanism to be contained functionally within the housing 234, and thereby help to stabilise the arm in balance at different retraction positions.

Figure 14:
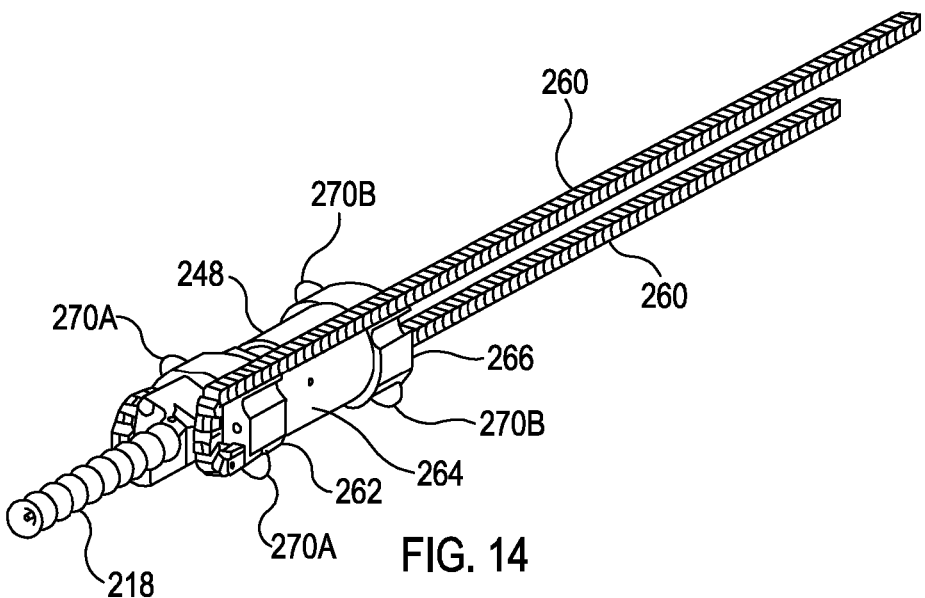
FIG. 14 is a front perspective view components of an anchoring arrangement.

FIG. 14 shows the shuttle unit 248 constituting a carriage to be disposed inside the support tube 240. The shuttle unit 248 comprises a generally tubular body 264 with a front cap 262 and a rear cap 266. The front cap 262 and the rear cap 266 are fixed to the tubular body 264 and thus rotationally and axially coupled.

Two energy chains 260 provide an extendable and retractable cable support and are configured to depend from the rear end 226 of support tube 240, covering the length of the support tube 240 to connect to a forward-facing side of the front cap 262 of the shuttle unit 248. The energy chains 260 accommodate wiring between the shuttle unit 248 and connectors at the rear end 226 of the support tube 240 and can retract to follow the position of the shuttle unit 248 within the support tube 240. It will be understood that the use of energy chains is exemplary. The energy chains 260 provide a cable carrying function reducing the risk of entrapment compared to free cables. However, other power supply and power connection means may be used. Conveniently, the energy chains 260 are provided at opposite sides of the shuttle unit 248, to fit into the void of the corners of two opposite edges of the support tube 240.

The shuttle unit 248 comprises a friction-reducing arrangement to facilitate translation along the support tube 240, in the form of two pairs of roller wheels 270A, 270B mounted on the shuttle unit 248. The first pair of the two pairs is constituted by front wheels 270A carried on the front cap 262, and the second pair of the two pairs is constituted by rear wheels 270B carried on the rear cap 266. The roller wheels 270 allow the shuttle unit 248 to roll inside the support tube 240. The roller wheels 270 are provided in the corners not occupied by the suspended ends of the energy chains 260 and therefore avoid interference with the energy chains 260. As such, the inner edges of the support tube 240 provide guide structures to prevent rotation of the shuttle unit 248 relative to the support tube 240. It will be apparent that although the quadrilateral cross-section is a convenient configuration allowing the flat walls to provide guide structures while also providing clearance for the energy chains 260, the invention is not necessarily limited in this regard and other arrangements may be used in other embodiments.

Figure 15:
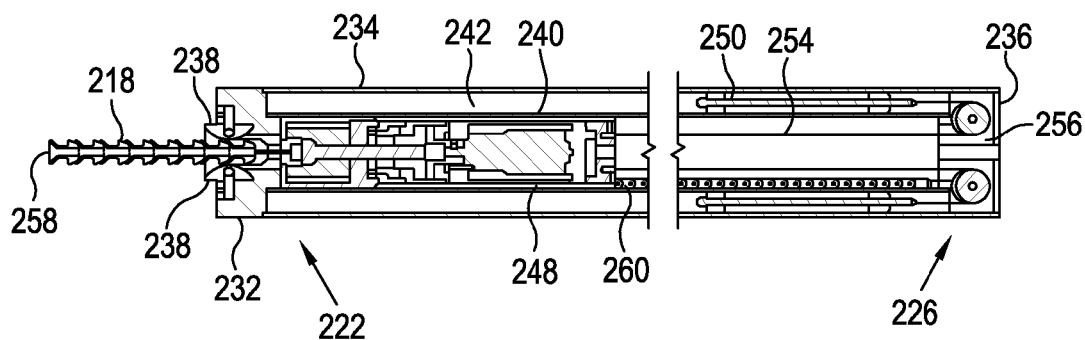
FIG. 15 is a longitudinal cross-section along the line C-C in FIG. 12B.

The configuration of the shuttle unit 248 within the support 210 is now described in general terms with reference to the cross-sectional FIG. 15. FIG. 15 shows the arrangement of the support tube 240 inside the housing 234, with the front cap 232, and the rear cap 236, and the gap 242 between the outside of the support tube 240 and the inside of the housing 234. The shuttle unit 248 is rollably disposed within the support tube 240 and connected to the counterweight 250 by the two wires 254 which run over the two pulleys 256. In this embodiment, while the shuttle unit is not prevented from moving (e.g. by a braking mechanism), the counterweight 250 has a tendency to move down (i.e., towards the front end 222 of the support 210) within the gap 242 and lifts the shuttle unit 248 upwards (i.e., towards the rear end 226 of the support 210) inside the support tube 240. The shuttle unit 248 can be pulled down against the force of the counterweight 250. However, this need not be the case in all embodiments, and other embodiments may utilise a counterweight in balance with the articulatable arm.

Also shown in FIG. 15 is a part of the articulatable arm 218 that is connected to and supported by the shuttle unit 248 and extends therefrom through the front cap 232 between the guide wheels 238. It will be appreciated that the articulatable arm 218 corresponds to the articulatable arm 18 and comprises a series of interconnecting elements that can be immobilised by way of a tensioning arrangement. The front end of the articulatable arm 218 provides a mounting arrangement for instrumentation or a device such as a lamp 120, and/or controls. Akin to the above embodiment, a wire 258 is provided as a tensioning element extending through hollow passages of the interconnecting elements of the articulatable arm 218 and anchored in a lead screw 288 (shown in FIG. 16A) of the shuttle unit 248. Preferably the tensioning arrangement allows tensioning the wire 258 without relying on a rotation thereof, such as by way of a lead screw nut acting on a lead screw to axially translate the lead screw without requiring lead screw rotation relative to the support tube 240.

The tensioning mechanism is operable between a locked configuration within the support tube 240 in which the articulatable arm 218 is immobilised, and a free configuration in which the wire 258 is extended sufficiently for the articulatable arm 218 to be moveable into any desired position.

Figure 16A:
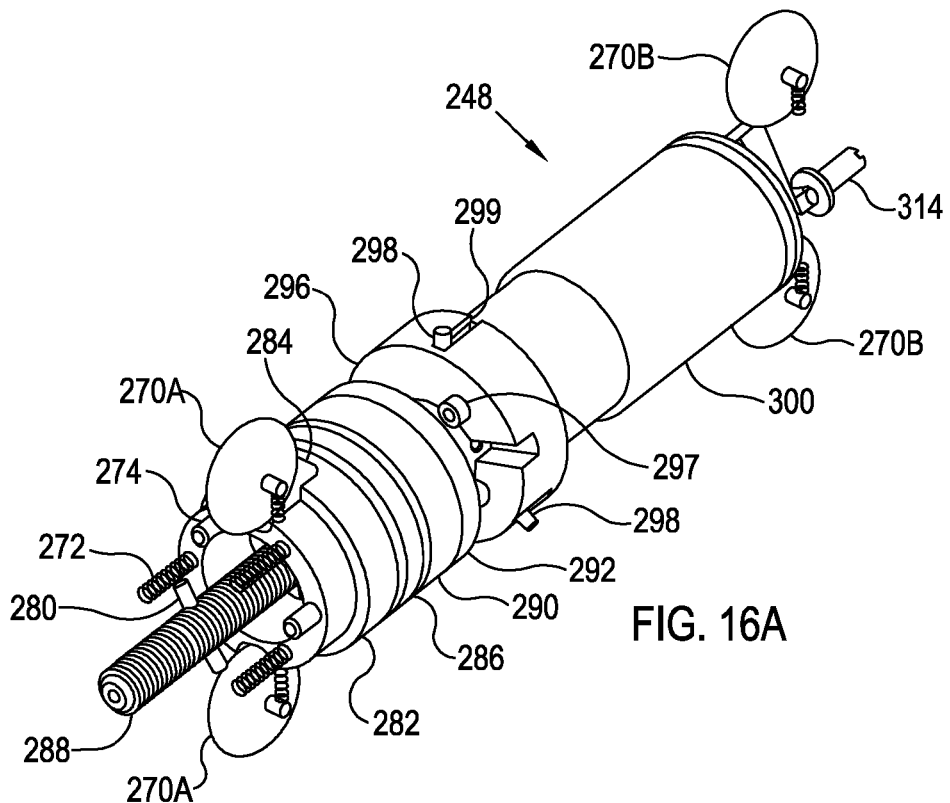
FIG. 16A is a front perspective view of a shuttle unit subassembly.

FIG. 16A shows internal components of the shuttle unit 248 relating to an exemplary retraction and immobilising mechanism. The assembly comprises a brake block 282, a thrust bearing 286 for transmitting axial force onto the brake block 282 from a lead screw nut 290 that is in threaded engagement with the lead screw 288, and an adapter 292 coupled to a motor/gear box 300. The motor/gear box 300 is attached on an anti-rotation collar 296. The brake block 282 comprises two locking wedges 284 which extend retractably below the front wheels 270A. Although not visible in FIG. 16A, FIG. 17B shows that the brake block 282 is axially spaced apart from the front cap 262 and that the anti-rotation collar 296 is axially slidable within the tubular body 264.

Figure 16B:
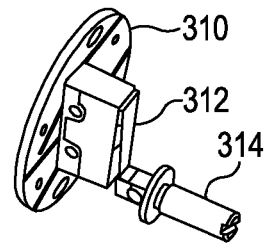
FIG. 16B is a rear perspective view of a part of a shuttle unit.

FIG. 16B shows a circuit board 310 located on the end cap 264 (see FIG. 14). The circuit board 310 is provided with a limit switch 312 and an adjustable anvil 314 which is configured to activate the limit switch 312. The roller wheels 270 are disposed on floating axles that are biased outwards, against the support tube 240, by an axle spring urging the roller wheels 270 into contact with the inner edges of the support tube 240.

Figure 18:
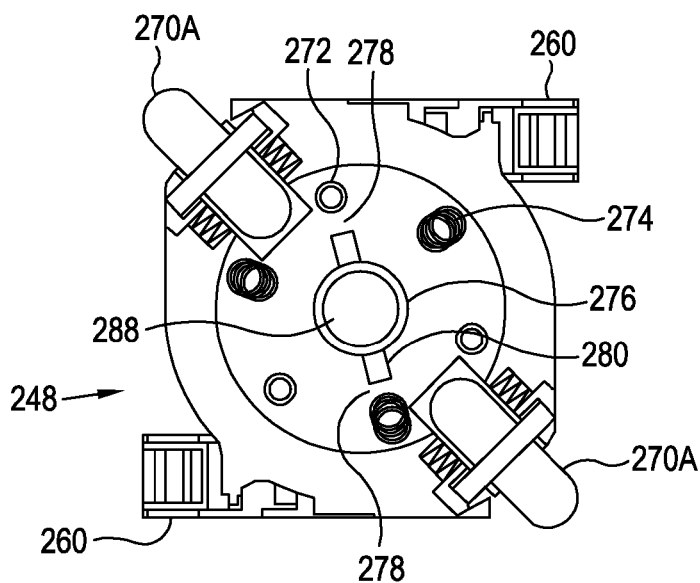
FIG. 18 shows a cross-section along the line D-D indicated in FIG. 17A.

FIG. 18 shows the inner, rearward-facing face of the front cap 262, which contains a series of compression springs 272 and a series of locating pins 274. The springs and pins protrude into the tubular body 264 (see FIGS. 17A and 17B) and extend into corresponding recesses within the brake block 282. Turning to FIGS. 17A and 17B, the brake block 282 is thus axially slidable on the locating pins 274, yet prevented from rotating relative thereto. The compression springs 272 protrude into corresponding recesses in the brake block 282. In its rest position, the brake block 282 is urged axially away from the front cap 262 by the compression springs 272 and thus prevented from acting on the front wheels 270A.

The front wheels 270A comprise high friction tyres of a suitable material to provide grip on the inside of the support tube 240 and on the locking ramps 284. The rear wheels 270B constitute support wheels to maintain alignment of the shuttle unit 248 within the support tube 240. The support wheels may also comprise high friction tyres.

As shown in FIGS. 17A, 17B and 18, the front cap 262 comprises a central bore 276 through which the lead screw 288 extends. On two opposite sides of the central bore 276 are laterally extending keyways 278 which accommodate an axially slidable anti-rotation pin 280. The anti-rotation pin 280 traverses through the lead screw 288 and thus the lead screw 288 is axially displaceable within the central bore 276 yet prevented from rotating relative to the front cap 262.

The above-mentioned anti-rotation collar 296 carrying the motor/gear box 300 comprises a series of radially spaced apart keyways 299 (shown in FIG. 16A) which engage with a series of corresponding radial pins 298 that are fixed on and protruding into the tubular body 264, as shown in FIG. 17B. The anti-rotation collar 296 is thus rotationally coupled with the tubular body 260 but axially displaceable. The motor/gear box 300 is fixed to the anti-rotation collar 296 by a series of fixtures 297 (see FIG. 16A). By way of this arrangement, the motor/gear box 300 can be held axially centred within the tubular body 264 while allowing the motor/gear box 300 to key axially into and out of the keyways 299.

The assembly is thus configured to maintain the motor/gear box 300, the tubular body 264, the front cap 262, the rear cap 266, and the lead screw 288 rotationally coupled, while allowing axial travel of the motor/gear box 300 and the lead screw 288 relative to each other and relative to the tubular body 264.

FIGS. 17A and 17B show the lead screw 288 carrying, in threaded engagement, a lead screw nut 290. The output shaft 302 of the motor/gear box 300 is connected to the lead screw nut 290 via the above-mentioned adapter 292. The adapter 292 comprises a central, forward-facing recess 294. The lead screw nut 290 acts on the thrust bearing 286 which abuts the brake block 282.

Torque from the motor/gear box 300 can thus be transmitted via the output shaft 302 and the adapter 292 to the lead screw nut 290. Upon rotation, the lead screw nut 290 advances axially along the lead screw 288, the lead screw 288 being prevented from rotating, and bears against the thrust bearing 286, which in turn transmits axial force onto the brake block 282 and thereby urges the brake block 282 forward against the force of the compression springs 272. This pushes the locking ramps 284 forward and against the front wheels 270A, thereby preventing rotation of the front wheels 270A. At the same time, the locking ramps 284 also splay the two front wheels 270A outward against the opposite edges of the support tube 240. The ensuing friction prevents the shuttle unit 248 from sliding and thus locks the shuttle unit 248 in its axial position.

Akin to the above embodiment for horizontal mounting, the pitch of the lead screw 288 can be chosen according to transmission requirements. To provide illustrative examples, the thread may have a 2 mm pitch and a diameter of 10 mm. The lead screw 288 is made from stainless steel. The lead screw nut 290 is made from low friction plastic. However, it will be appreciated that the invention is not so limited and that other component materials and dimensions may be used.

As shown in FIG. 17A, the lead screw nut 290 and the adapter 292 are rigidly connected to one another by fixtures 291. Likewise, the adapter 292 is attached to motor shaft 302. Thus, because the keyways 299 allow axial movement of the anti-rotation collar 296 relative to the radial pins 298, the motor/gear box 300 is pulled axially by the lead screw nut 290 as it advances on lead screw 288. The forward movement of the brake block 296 is limited by the front end of the locking ramps 284 abutting against the inner surface of the front cap 262.

Once the brake block 282 abuts against the front cap 262, further torque from the output shaft 302 does not advance the lead screw nut 290 towards the front cap 262. Instead, because the lead screw 288 is prevented from rotating relative to the tubular body 264 and the motor/gear box 300, further rotation of the lead screw nut 290 pulls the lead screw 288 backwards, while the thrust bearing 286 continues to bias against the brake block 282.

As the lead screw 288 is pulled back into the recess 294 of the adapter 292, the wire 258 is tensioned and the segments of the articulatable arm 218 are locked in position.

To unlock the articulatable arm 218, the motor/gear box 300 rotates in the opposite sense to the locking sense. Thus, rotation of the lead screw nut 290 causes the lead screw 288 to be advanced. As the lead screw 288 is advanced forward, the wire 254 relaxes, causing the articulatable arm 218 to unlock and relax. The motor/gear box 300, the lead screw nut 290, and the brake block 282 are moved backwards until the radial pins 298 abut against the end of their respective key ways 299 and thereby prevent further rearward travel of the motor/gear box 300. The pulling back of the brake block 282 unblocks the front wheels 270A and allows the shuttle unit 248 to roll within the support tube 240.

Once the motor/gear box 300 has fully retracted, the anvil 314 abuts against the rear cap 236 which in turn contacts the switch 312. This activates a control signal to stop the motor/gear box 300 and to terminate any power or control signals routed via the rear cap 236. Thus, both the front wheels 270A and the articulatable arm 218 are fully unlocked and pulled upwards by the counterweight 250. In this condition, the articulatable arm 218 is ready to be re-positioned.

FIGS. 19A and 19B show two photographs a prototype 400 immobilised in different configurations. The same numerals are used for FIGS. 19A and 19B. The prototype 400 comprises three articulatable arms 418A, 418B, 418C retractably anchored to a ceiling mount 416A, 416B, 416C, respectively. The ceiling mounts 416A, 416B, 416C, correspond to the vertically installed support 210 described above, only the front caps being visible. Each of the three articulatable arms 418A, 418B, 418C comprises a retracting mechanism and a tensioning mechanism allowing the arms to be immobilised. The three articulatable arms 418A, 418B, 418C carry a lamp body 420 comprising an actuator 430 that actuates the tensioning mechanism and the retracting mechanism. FIGS. 19A and 19B show the same lamp body 420, however each FIGS. 19A and 19B shows the lamp body 420 at a different position. Relative to FIG. 19A, FIG. 19B shows the articulatable arms 418A, 418B, 418C retracted further into the ceiling mount such that the external arms portions thereof are shorter. In both FIGS. 19A and 19B, the articulatable arms are tensioned to be immobilised, as can be appreciated from the somewhat contorted configuration, such that the lamp body 420 does not loosely hang from the ceiling at a centre of gravity, but remains in the position and orientation set by a user. The articulatable arms 418A, 418B, 418C are, in the immobilised configuration, relatively rigid and so may remain in position even if they are accidentally knocked. If the lamp body 420 is to be repositioned, this can be achieved single-handedly with relatively little effort via the actuator 430 to unlock the immobilising mechanism. The immobilising mechanism ensures that the lamp 420 is held in the position for the duration of several hours, and practically any length of time, as may be required during surgery. The brake mechanisms and immobilising mechanisms are configured such that they remain immobilised in the absence of power supply, although it will be appreciated that other configurations may be used in some embodiments.

The exemplary embodiments comprise three articulatable arms for a single lamp. However, the invention is not necessarily so limited and depending on the mass of the equipment and strength of the retraction system and tensioning system, fewer or more arms may be required. In some embodiments, a single support arm may suffice to reliably support a device.

It will be appreciated that various modifications may be made to the above embodiments without departing from the scope of the present invention as defined by the appended claims.

The invention claimed is:

1. An adjustable support arm system comprising:
an anchoring arrangement for mounting the support arm system to a structure;
an arm carried by the anchoring arrangement and comprising a plurality of arm segments articulatable between several arm positions, the arm being configured to support a device, and
an immobilising mechanism operable between a free configuration and a locked configuration, wherein in the free configuration the immobilising mechanism permits movement of the articulatable arm, and wherein in the locked configuration the immobilising mechanism maintains the articulatable arm in one of the several arm positions; and
a retracting mechanism to retract the arm at least partially into a housing structure provided by the anchoring arrangement,
wherein the immobilising mechanism comprises a locking means to maintain the plurality of arm segments immobilised in the locked configuration,
wherein the support arm system further comprises an actuator located at one of a location along the articulatable arm and a location at an end of the articulatable arm, the actuator allowing the locking means to be released, and
wherein the retracting mechanism is operatively connected with the actuator such that, upon releasing the locking means, the retracting mechanism is released to permit extension or retraction of the articulatable arm.

2. The support arm system according to claim 1, wherein the anchoring arrangement comprises a stabilising system to maintain the arm in balance at different retraction positions.

3. The support arm system according to claim 2, wherein the stabilising system comprises a counterbalancing system.

4. The support arm system according to claim 1, wherein the housing structure comprises a guide channel from which the articulatable arm extends.

5. The support arm system according to claim 4, wherein the guide channel is provided by one of a guide funnel and guide wheels.

6. The support arm system according to claim 1, wherein the arm comprises a plurality of interconnected elements, connected in series to form a length of arm.

7. The support arm system according to claim 6 wherein the interconnected elements are inside a skin structure.

8. The support arm system according to claim 7, wherein the interconnected elements are angularly disposable relatively to each other by ball joint connections.

9. The support arm system according to claim 6, wherein the interconnected elements comprise a channel passage for end-to-end connection of a series of interconnected elements.

10. The support arm system according to claim 9, wherein the channel passage extends axially within the interconnected elements.

11. The support arm system according to claim 6, wherein the interconnected elements are connected by a tensionable arrangement.

12. The support arm system according to claim 11, wherein the tensionable arrangement comprises one of a wire, a cable, and a cord.

13. The support arm system according to claim 11, wherein the tensionable arrangement is tensionable by a tensioning mechanism disposed in the anchoring arrangement.

14. The support arm system according to claim 1, wherein the anchoring arrangement comprises a motorised unit providing at least one of a retracting mechanism and a tensioning mechanism.

15. The support arm system according to claim 1, comprising a plurality of anchoring arrangements and arms to support one device.

16. The support arm system according to claim 1, wherein the device is a lamp.

* * * * *